United States Patent
Reynes et al.

(10) Patent No.: US 8,435,777 B1
(45) Date of Patent: May 7, 2013

(54) CPG-FREE GENE FOR A NEW SECRETED REPORTER PROTEIN

(75) Inventors: Jean Paul Reynes, Escalquens (FR); Céline Casteran, Toulouse (FR); Daniel Drocourt, Saint-Orens de Gameville (FR); Gérard Tiraby, Toulouse (FR)

(73) Assignee: Cayla, Toulouse (FR)

( * ) Notice: Subject to any disclaimer, the term of this patent is extended or adjusted under 35 U.S.C. 154(b) by 0 days.

(21) Appl. No.: 13/354,469

(22) Filed: Jan. 20, 2012

(51) Int. Cl.
  *C12N 9/02* (2006.01)
  *C12N 15/00* (2006.01)
  *C12N 15/74* (2006.01)

(52) U.S. Cl.
  USPC .......................... 435/189; 435/320.1; 435/476

(58) Field of Classification Search .................. None
  See application file for complete search history.

(56) References Cited

U.S. PATENT DOCUMENTS

| | | |
|---|---|---|
| 6,232,107 B1 | 5/2001 | Bryan et al. |
| 7,297,483 B2 | 11/2007 | Golz et al. |
| 2004/0219677 A1 | 11/2004 | Drocourt et al. |
| 2009/0233320 A1 | 9/2009 | Takenaka |
| 2010/0105090 A1 | 4/2010 | Golz et al. |
| 2010/0292307 A1* | 11/2010 | Hyde et al. .................. 514/44 R |
| 2012/0034672 A1 | 2/2012 | Kim et al. |

FOREIGN PATENT DOCUMENTS

| | | |
|---|---|---|
| WO | 9949019 | 9/1999 |
| WO | 0242470 | 5/2002 |
| WO | 02072846 | 9/2002 |
| WO | 2006061906 | 6/2006 |
| WO | 2010119721 | 10/2010 |
| WO | 2011002924 | 1/2011 |

OTHER PUBLICATIONS

Diegelmann J et al. Comparative Analysis of the lambda-interferons IL-28A and IL-29 regarding their transcriptome and their antiviral properties against Hepatitis C Virus. 2010. PLoS One. vol. 5 Issue 12 p. 1-13.*
Haugwitz M et al. Multiplexing bioluminescent and fluorescent reporters to monitor live cells. 2008. Current Chemical Genomics. 1. p. 11-19.*
Promega Technical Bulletin. Luciferase Assay System. Revised form Dec. 2011. p. 1-17.*

* cited by examiner

*Primary Examiner* — Manjunath Rao
*Assistant Examiner* — Paul Holland
(74) *Attorney, Agent, or Firm* — Young & Thompson

(57) ABSTRACT

A synthetic gene devoid of CpG nucleotide derived by genetic engineering from copepod luciferases genes that code for a new secreted luciferase with a strong bioluminescent signal. This gene display advantageous properties to be used as a reporter genes in cell based assays.

20 Claims, 8 Drawing Sheets

```
G-luc    ATGGGAGTCAAGGTGCTGTTTGCCCTCATCTGTATTGCTGTTGCTGAGGCAAAACCCACT 60
Mp-luc1  ATGGAAATCCAGGTGCTGTTTGCCCTCATCTGCTTTGCCCTGGTGCAGGCCAACCCCACT 60
Ml-luc   ATGGACATTAAGGTGGTGTTCACCCTGGTCTTCTCTGCCCTGGTGCAGGCCAAGAGCACT 60
Mp-luc2  ATGGGAGTCAAGCTGATCTTTGCTGTGGTCTGTGTGGCAGCAGCTCAGGCAGCAACCATC 60
         ****   *  ** **  * **    *   ***    **    *  ****    **

G-luc    ---GAAAACAATGAAGACTTCAATATAGTTGCTGTGGCCTCCAACTTTGCCACCACAGAC 117
Mp-luc1  ---GAAAACAAGGATGACATTGACATAGTTGGGGTGGAGGGCAAGTTTGGCACCACTGAC 117
Ml-luc   ---GAATTTGACCCCAACATTGACATAGTTGGCCTTGAGGGCAAGTTTGGGATCACCAAC 117
Mp-luc2  AATGAAAACTTTGAGGACATTGACCTGGTTGCCATTGGAGGCTCCTTTGCA---CTGGAT 117
            ***        **  *  *  * ****  *  *    *    ****      *

G-luc    CTT--------------------------------------------------------- 120
Mp-luc1  CTTGAGACTGACCTGTTCACCATTGTGGAGGACATGAATGTGATTAGC------------- 165
Ml-luc   CTGGAGACAGACCTCTTCACCATCTGGGAGACCATGGAGGTGATGATCAAGGCTGACATT 177
Mp-luc2  GTTGATGCCAAC------------------------------------------------ 129
          *

G-luc    ---------------------------------------------DATGCTGACAGGGGCAAG 138
Mp-luc1  ------------------AGGGACACAAACCTGGCCAACTCAGATGCTGACAGGGGCAAG 207
Ml-luc   GCTGACACTGACAGGGCTAGTAACTTTGTGGCGACAGAGACAGATGCTAACAGGGGCAAG 237
Mp-luc2  ------------------AGGGGA------------------------GGTCATGGGGGCCAC 150
                                                    *  *   ***** *

G-luc    CTGCCTGGCAAAAAACTCCCCCTAGAAGTCCTGAAGGAGATGGAGGCCAATGCCAGAAAG 198
Mp-luc1  ATGCCTGGCAAAAAACTCCCCCTAGAAGTCCTGATTGAGATGGAGGCCAATGCCAGAAAG 267
Ml-luc   ATGCCTGGCAAAAAACTCCCCCTAGCTGTCATCATGGAGATGGAGGCCAATGCCTTCAAG 297
Mp-luc2  ---CCTGGCAAAAAAATGCCCAAAGAGGTCCTGGTGGAGATGGAGGCCAATGCCAAAAGG 207
            ***********  *****  **   *** *    *****************    * *

G-luc    GCTGGTTGCACAAGAGGCTGCCTCATTTGCCTCTCCCACATTAAGTGCACCCCCAAGATG 258
Mp-luc1  GCTGGTTGCACAAGAGGCTGCCTCATTTGCCTCAGCCACATTAAGTGCACAGCCAAGATG 327
Ml-luc   GCTGGTTGCACAAGAGGCTGCCTCATTTGCCTCTCCAAGATTAAGTGCACAGCCAAGATG 357
Mp-luc2  GCTGGTTGCCACAGAGGCTGCCTCATTTGCCTCAGCCACATTAAGTGCACCAAGAAGATG 267
         *********  ******************** *  *  * **********    ******

G-luc    AAGAAATTTATCCCTGGCAGGTGCCACACTTATGAAGGTGACAAGGAGTCTGCTCAGGGA 318
Mp-luc1  AAGGTCTACATCCCTGGCAGGTGCCATGACTATGGGGTGACAAGAAGACTGGTCAGGGA 387
Ml-luc   AAGGTCTACATCCCTGGCAGGTGCCATGACTATGGGGGTGACAAGAAGACTGGTCAGGCA 417
Mp-luc2  AAGAAATTTATCCCTGGCAGGTGCCACTCTTATGAAGGTGACAAGGACTCTGCTCAGGGA 327
         ***   *  **************** *    ****  ********  *   *** ***** *

G-luc    GGGATTGGAGAGGCAATTGTTGATATCCCAGAGATTCCTGGCTTCAAGGATTTGGAGCCA 378
Mp-luc1  GGGATTGTTGGGGCAATTGTTGATATCCCAGAGATTAGTGGCTTCAAGGAGCTGGGGCCA 447
Ml-luc   GGGATTGTGGGGGCAATTGTTGATATCCCAGAGATTAGTGGCTTCAAGGAGATGCCCCA 477
Mp-luc2  GGGATTGGAGAGGAAATTGTTGATATGCCAGAGATTCCTGGCTTCAAGGATAAGGAGCCA 387
         *******  *  ** **********  ******** ** ************    * ***

G-luc    ATGGAACAGTTTATTGCTCAAGTGGACCTCTGTGTGGATTGCACCACTGGCTGTCTGAAG 438
Mp-luc1  ATGGAGCAGTTTATTGCTCAAGTGGACCTCTGTGCTGATTGCACCACTGGCTGTCTGAAG 507
Ml-luc   ATGGAGCAGTTTATTGCTCAAGTGGACAGGTGTGCTTCCTGCACCACTGGCTGTCTGAAG 537
Mp-luc2  ATGGACCAGTTTATTGCTCAAGTGGACCTCTGTGTGGATTGCACCACTGGCTGTCTGAAG 447
         *****  *******************     ****            *********************

G-luc    GGCCTTGCCAATGTCCAGTGCTCTGACCTCCTGAAGAAGTGGCTTCCCCAGAGGTGTGCC 498
Mp-luc1  GGCCTTGCCAATGTCAGTGCTCTGCCCTCCTGAAGAAGTGGCTTCCAGACAGGTGTGCC 567
Ml-luc   GGCCTTGCCAATGTCAGTGCTCTGAGCTCCTGAAGAAGTGGCTTCCTGACAGGTGTGCC 597
Mp-luc2  GGCCTTGCCAATGTCCACTGCTCTGACCTCCTGAAGAAGTGGCTTCCCAGCAGGTGTAAG 507
         ***************  *  ******* ******************      *****

G-luc    ACTTTTGCCAGCAAGATTCAGGGTCAGGTGGACAAAATCAAGGGTGCAGGTGGGGACTGATGA 561
Mp-luc1  TCTTTTGCTGACAAGATTCAGTCTGAGGTGGACAACATCAAGGGTCTGGCTGGGGACAGATGA 630
Ml-luc   TCTTTTGCTGACAAGATTCAGAAGGAGGTGCACAACATCAAGGGTATGGCTGGGGACAGATGA 660
Mp-luc2  ACTTTTGCCTCCAAGATTCAGAGTCAGGTGGACACAATCAAGGGTCTGGCTGGGGACAGATGA 570
         *******  ********** *****  ***  *********  * ******* *****
```

FIG. 1

```
OL01  5' ACAGTAGCTTCCACCATGGAANTCNAGNTG 3'                                 (SEQ ID NO:14)
OL03  NTGTTTGCCNTCNTCTGTNTTGCTNTTNCTNAGGCANAANCCACTGAANTCNATNAANAC          (SEQ ID NO:15)
OL05  NTCNATATAGTTNCTNTGNCCNCCNACTTTNCCACCACANATCTTGAGNCTNACCTGTTC          (SEQ ID NO:16)
OL07  ACCATCNGGGAGNCCATGNATGTGATTAGCAGTGACACANAGNTGNTGNACNCAGATGCT          (SEQ ID NO:17)
OL09  NACAGGGGCNAGNTGCCTGGCAAAAAACTCCCCNTANATGTCNTGNTGGAGNTGGAGGCC          (SEQ ID NO:18)
OL11  AATGCCNGANGGGCTGGTTGCNCAAGAGGCTGCCTCATTTGCCTCNCCNACATTAAGTGC          (SEQ ID NO:19)
OL13  ACCNCTAAGATGAAGNAANTTATCCCTGGCAGGTGCCACNCTTATNAAGGTGACAAGNAG          (SEQ ID NO:20)
OL15  NCTNCTCAGNGACGGATTNGANAGGCAATTGTTGATATCCCAGAGATTNCTGGCTTCAAG          (SEQ ID NO:21)
OL17  NATNAGNAGCCANTGNACCAGTTTATTGCTCAAGTGGACNTCTGTNCTNATTGCACCCACT         (SEQ ID NO:22)
OL19  GGCTGTCTGAAGGGCCTTGCCAATGTCNAGTGCTCTNACCTCCTGAAGAAGTGGCTTCCC          (SEQ ID NO:23)
OL21  NAGAGGTGTNCCNCTTTTGCCNGCAAGATTCAGNGTNAGGTGNACNAAATCAAGGGTNTG          (SEQ ID NO:24)
OL23  NCTGGGGACNGATGATAGCTAGCTGGCCAG                                        (SEQ ID NO:25)

OL02  5' AGNAANAGCAANACAGANGANGGCAAACANCANCTNGANTTCCATGGTGGAAGCTACTGT 3'    (SEQ ID NO:26)
OL04  AAAGTNGGNGGNCANAGNAACTATATNGANGTNTTNATNGANTTCAGTGGNTTNTGCCTN          (SEQ ID NO:27)
OL06  GCTAATCACATNCATGGNCTCCCNGATGGTGAACAGGTNAGNCTGAAGATNTGTGGTGGN          (SEQ ID NO:28)
OL08  GAGTTTTTTGCCAGGCANCTNGCCCCTGTNAGCATCTGNGTNCANCANCTNTGTGTCACT          (SEQ ID NO:29)
OL10  GCCTCTTGNGCAACCAGCCCNTCNGGCATTGGCCTCCANCTCCANCANGACATNTANGGG          (SEQ ID NO:30)
OL12  GCCAGGGATAANTTNCTTCATCTTAGNGGTGCACTTAATGTNGGNGAGGCAAATGAGGCA          (SEQ ID NO:31)
OL14  AATTGCCTNTCNAATCCCTCNCTGAGNAGNCTNCTTGTCACCTTNATAAGNGTGGCACCT          (SEQ ID NO:32)
OL16  AGCAATAAACTGGTNCANTGGCTNCTNATNCTTGAAGCCAGNAATCTCTGGGATATCAAC         (SEQ ID NO:33)
OL18  CTNGACATTGCCAAGGCCCTTCAGACAGCCAGTGGTGCAATNAGNACAGANGTCCACTTG          (SEQ ID NO:34)
OL20  AATCTTGCNGGCAAAAGNNGGNACACCTCTGGGAAGCCACTTCTTCAGGAGGTNAGAGCA          (SEQ ID NO:35)
OL22  CTGGCCAGCTAGCTATCATCNGTCCCCAGNCANACCCTTGATTTNGTNCACCTNACNCTG         (SEQ ID NO:36)
```

FIG. 2

```
ATGGAAATCAAGGTGCTGTTTGCCCTCATCTGTATTGCTGTTGCTGAGGCAAAACCCACT  60
GAAATCAATGAAGACCTCAATATAGCTGCTGTGGCCTCCAACTTTGCCACCACAGATCTT  120
GAGACTGACCTGTTCACCAACTGGGAGACCATGAATGTGATTAGCACTGACACAGAGCAG  180
GTGAACACAGATGCTGACAGGGGCAAGCTGCCTGGCAAAAAACTCCCCCCAGATGTCCTG  240
AGGGAGCTGGAGGCCAATGCCAGAAGGGCTGGTTGCACAAGAGGCTGCCTCATTTGCCTC  300
TCCCACATTAAGTGCACCCCTAAGATGAAGAAATTTATCCCTGGCAGGTGCCACACTTAT  360
GAAGGTGAAAAGGAGTCTGCTCAGGGAGGGATTGGAGAGGCAATTGTTGATATCCCAGAG  420
ATTCCTGGCTTCAAGGATAAGGAGCCACTGGACCAGTTTATTGCTCAAGTGGACCTCTGT  480
GCTGATTGCACCACTGGCTGTCTGAAGGGCCTTGCCAATGTCCAGTGCTCTGACCTCCTG  540
AAGAAGTGGCTTCCCCAGAGGTGTACCACTTTTGCCAGCAAGATTCAGGGTAGGGTGGAC  600
AAAATCAAGGGTCTGGCTGGGACAGATGA  630
```

FIG. 3

```
Met Glu Ile Lys Val Leu Phe Ala Leu Ile Cys Ile Ala Val Ala Glu Ala Lys Pro Thr  20
Glu Ile Asn Glu Asp Leu Asn Ile Ala Ala Val Ala Ser Asn Phe Ala Thr Thr Asp Leu  40
Glu Thr Asp Leu Phe Thr Asn Trp Glu Thr Met Asn Val Ile Ser Thr Asp Thr Glu Gln  60
Val Asn Thr Asp Ala Asp Arg Gly Lys Leu Pro Gly Lys Lys Leu Pro Pro Asp Val Leu  80
Arg Glu Leu Glu Ala Asn Ala Arg Arg Ala Gly Cys Thr Arg Gly Cys Leu Ile Cys Leu 100
Ser His Ile Lys Cys Thr Pro Lys Met Lys Lys Phe Ile Pro Gly Arg Cys His Thr Tyr 120
Glu Gly Glu Lys Glu Ser Ala Gln Gly Gly Ile Gly Glu Ala Ile Val Asp Ile Pro Glu 140
Ile Pro Gly Phe Lys Asp Lys Glu Pro Leu Asp Gln Phe Ile Ala Gln Val Asp Leu Cys 160
Ala Asp Cys Thr Thr Gly Cys Leu Lys Gly Leu Ala Asn Val Gln Cys Ser Asp Leu Leu 180
Lys Lys Trp Leu Pro Gln Arg Cys Thr Thr Phe Ala Ser Lys Ile Gln Gly Arg Val Asp 200
Lys Ile Lys Gly Leu Ala Gly Asp Arg 209
```

FIG. 4

```
Lucia    -MEIKVLFALICIAVAEAKPT-EINEDLNIAAVASNFATTDLETDLFTNWETMNV-IS--  55
Mp-luc2  -MGVKLIFAVVCVAAAQAATINENFEDIDLVAIGGSFAL-DVDAN--------------  43
G-luc    -MGVKVLFALICIAVAEAKPT-ENNEDFNIVAVASNFATTDLD----------------  41
Mp-luc1  MMEIQVLFALICFALVQANPT-ENKDDIDIVGVEGKFGTTDLETDLFTIVEDMNV-IS--  56
Ml-luc   -MDIKVVFTLVFSALVQAKST-EFDPNIDIVGLEGKFGITNLETDLFTIWETMEVMIKAD 58
          *  ::::*:::   *  .:*  .   *    .:::  .:   ..*.   :::

Lucia    -------TDTEQVNTDADRGKLPGKKLPPDVLRELEANARRAGCTRGCLICLSHIKCTPK 108
Mp-luc2  ---------------RGGHGGHPGKKMPKEVLVEMEANAKRAGCHRGCLICLSHIKCTRK  88
G-luc    ---------------ADRGKLPGKKLPLEVLKEMEANARKAGCTRGCLICLSHIKCTPK   85
Mp-luc1  -------RDTNLANSDADRGKMPGKKLPLEVLIEMEANARKAGCTRGCLICLSKIKCTAK 109
Ml-luc   IADTDRASNFVATETDANRGKMPGKKLPLAVIMEMEANAFKAGCTRGCLICLSKIKCTAK 118
          ..:*  ****:*  *:  *:****  :***  ********:**** *

Lucia    MKKFIPGRCHTYEGEKESAQGGIG-EAIVDIPEIPGFKDKEPLDQFIAQVDLCADCTTGC 167
Mp-luc2  MKKFIPGRCHSYEGDKDSAQGGIG-EEIVDMPEIPGFKDKEPMDQFIAQVDLCVDCTTGC 147
G-luc    MKKFIPGRCHTYEGDKESAQGGIG-EAIVDIPEIPGFKDLEPMEQFIAQVDLCVDCTTGC 144
Mp-luc1  MKVYIPGRCHDYGGDKKTGQAGIV-GAIVDIPEISGFKELGPMEQFIAQVDLCADCTTGC 168
Ml-luc   MKVYIPGRCHDYGGDKKTGQAGIV-GAIVDIPEISGFKEMAPMEQFIAQVDRCASCTTGC 177
         **  :******  *  ***.:.*.**    ***:***.***:   *:;********  *  *****

Lucia    LKGLANVQCSDLLKKWLPQRCTTFASKIQGRVDKIKGLAGDR 209
Mp-luc2  LKGLANVHCSDLLKKWLPSRCKTFASKIQSQVDTIKGLAGDR 189
G-luc    LKGLANVQCSDLLKKWLPQRCATFASKIQGQVDKIKGAGGD- 185
Mp-luc1  LKGLANVKCSALLKKWLPDRCASFADKIQSEVDNIKGLAGDR 210
Ml-luc   LKGLANVKCSELLKKWLPDRCASFADKIQKEVHNIKGMAGDR 219
         ********:** ******* **  :**.***  :**..***  .**
```

FIG. 5

```
Lys Pro Thr Glu Ile Asn Glu Asp Leu Asn Ile Ala Ala Val Ala Ser Asn Phe Ala Thr  20
Thr Asp Leu Glu Thr Asp Leu Phe Thr Asn Trp Glu Thr Met Asn Val Ile Ser Thr Asp  40
Thr Glu Gln Val Asn Thr Asp Ala Asp Arg Gly Lys Leu Pro Gly Lys Lys Leu Pro Pro  60
Asp Val Leu Arg Glu Leu Glu Ala Asn Ala Arg Arg Ala Gly Cys Thr Arg Gly Cys Leu  80
Ile Cys Leu Ser His Ile Lys Cys Thr Pro Lys Met Lys Lys Phe Ile Pro Gly Arg Cys 100
His Thr Tyr Glu Gly Glu Lys Glu Ser Ala Gln Gly Gly Ile Gly Glu Ala Ile Val Asp 120
Ile Pro Glu Ile Pro Gly Phe Lys Asp Lys Glu Pro Leu Asp Gln Phe Ile Ala Gln Val 140
Asp Leu Cys Ala Asp Cys Thr Thr Gly Cys Leu Lys Gly Leu Ala Asn Val Gln Cys Ser 160
Asp Leu Leu Lys Lys Trp Leu Pro Gln Arg Cys Thr Thr Phe Ala Ser Lys Ile Gln Gly 180
Arg Val Asp Lys Ile Lys Gly Leu Ala Gly Asp Arg 192
```

FIG. 6

```
SLuc    ATGGAAATCAAGGTGCTGTTTGCCCTCATCTGTATTGCTGTTGCTGAGGCAAAACCCACT 60
G-luc   ATGGGAGTCAAGGTGCTGTTTGCCCTCATCTGTATTGCTGTTGCTGAGGCAAAACCCACT 60
hGLuc   ATGGGAGTCAAAGTTCTGTTTGCCCTGATCTGCATCGCTGTGGCCGAGGCCAAGCCCACC 60
        ****  * **** **  *********** ***** **  ***** **  ***** ** *****

SLuc    GAAATCAATGAAGACCTCAATATAGCTGCTGTGGCCTCCAACTTTGCCACCACAGATCTT 120
G-luc   GAAAACAATGAAGACTTCAATATAGTTGCTGTGGCCTCCAACTTTGCCACCACAGACCTT 120
hGLuc   GAGAACAACGAAGACTTCAACATCGTGGCCGTGGCCAGCAACTTCGCGACCACGGATCTC 120
        ** * ***  ****** ****  **  *  ** ****** ****** **  *****  ** **

SLuc    GAGACTGACCTGTTCACCAACTGGGAGACCATGAATGTGATTAGCACTGACACAGAGCAG 180
G-luc   GA---------------------------------------------------------- 122
hGLuc   GA---------------------------------------------------------- 122
        **

SLuc    GTGAACACAGATGCTGACAGGGGCAAGCTGCCTGGCAAAAAACTCCCCCCAGATGTCCTG 240
G-luc   -----------TGCTGACAGGGGCAAGCTGCCTGGCAAAAAACTCCCCCTAGAAGTCCTG 171
hGLuc   -----------TGCTGACCGCGGGAAGTTGCCCGGCAAGAAGCTGCCCGCTGGAGGTGCTC 171
                    ******* * **  ***  ****  *****  **  **  *   ** ** **

SLuc    AGGGAGCTGGAGGCCAATGCCAGAAGGGCTGGTTGCACAAGAGGCTGCCTCATTTGCCTC 300
G-luc   AAGGAGATGGAGGCCAATGCCAGAAAGGCTGGTTGCACAAGAGGCTGCCTCATTTGCCTC 231
hGLuc   AAACAGATGGAAGCCAATGCCCGGAAAGCTGCTGCACCAGGGGCTGTCTGATCTGCCTG 231
         *    ***  **** *********  *   *  *****  ***** ** ** *****

SLuc    TCCCACATTAAGTGCACCCCTAAGATGAAGAAATTTATCCCTGGCAGGTGCCACACTTAT 360
G-luc   TCCCACATTAAGTGCACCCCCAAGATGAAGAAATTTATCCCTGGCAGGTGCCACACTTAT 291
hGLuc   TCCCACATCAAGTGCACGCCCAAGATGAAGAAGTTCATCCCAGGACGCTGCCACACCTAC 291
        ******** ********  **  ************  **  *****  *  ******** *

SLuc    GAAGGTGAAAAGGAGTCTGCTCAGGGAGGGATTGGAGAGGCAATTGTTGATATCCCAGAG 420
G-luc   GAAGGTGACAAGGAGTCTGCTCAGGGAGGGATTGGAGAGGCAATTGTTGATATCCCAGAG 351
hGLuc   GAAGGCGACAAAGAGTCCGCACACAGGCGGCATAGGCGAGGCGATCGTCGACATTCCTGAG 351
        ***** ** **  *****  **    *  ** **  *  *****  ** ** **   ** **

SLuc    ATTCCTGGCTTCAAGGATAAGGAGCCACTGGACCAGTTTATTGCTCAAGTGGACCTCTGT 480
G-luc   ATTCCTGGCTTCAAGGATTTGGAGCCAATGGAACAGTTTATTGCTCAAGTGGACCTCTGT 411
hGLuc   ATTCCTGGGTTCAAGGACTTGGAGCCTATGGAGCAGTTCATCGCACAGGTCGATCTGTGT 411
        ********  *******    ***  *  ****  ***** ** ** **  ** ** ***

SLuc    GCTGATTGCACCACTGGCTGTCTGAAGGGCCTTGCCAATGTCCAGTGCTCTGACCTCCTG 540
G-luc   GTGGATTGCACCACTGGCTGTCTGAAGGGCCTTGCCAATGTCCAGTGCTCTGACCTCCTG 471
hGLuc   GTGGACTGCACAACTGGCTGCCTCAAAGGGCTTGCCAACGTGCAGTGTTCTGACCTGCTC 471
        *  ** ***** ********  ** ** ***** *****  **  ***** ******** **

SLuc    AAGAAGTGGCTTCCCCAGAGGTGTACCACTTTTGCCAGCAAGATTCAGGGTAGGGTGGAC 600
G-luc   AAGAAGTGGCTTCCCCAGAGGTGTGCCACTTTTGCCAGCAAGATTCAGGGTCAGGTGGAC 531
hGLuc   AAGAAGTGGCTGCCGCAACGCTGTGCGACCTTTGCCAGCAAGATCCAGGGCCAGGTGGAC 531
        *********** ** ** *   *** ** *************  ****** *******

SLuc    AAAATCAAGGGTCTGGCTGGGGACAGATGA 630
G-luc   AAAATCAAGGGTGCAGGTGGGGACTGA--- 558
hGLuc   AAGATCAAGGGGGCCGGTGGTGACTAA--- 558
        ** ********   *** *** ***  *
```

FIG. 7

```
GCTGAATTAGTTTCACTTTCCAGTTTCAGTTTCCAGTTTCATTTTCCAGTTTCATTTTCC   60
AGTTTCATTTTCCTGATATCCTGCAGGAAAAAGAGTCCTCTAAAGTATAATAAAAAGAAA  120
AAAAGAAAAAGAGTCCTGCCAATTTCACTTTCTAGTTTCACTTTCCCTTTTGTAATGTCA  180
GCTGAAGGGAAACAAACAAAAAGGAACCAGAGGCCACTTGTATATATAGGTCTCTTCAGC  240
ATTTATTGGTGGCAGAAGAGGAAGATTTCTGAAGAGTGCAGCTGCCTGAACTGAGCCCTG  300
CTGAACAGCTGAGAATTGCACTGCAACCATGGAAATCAAGGTGCTGTTTGCCCTCATCTG  360
TATTGCTGTTGCTGAGGCAAAACCCACTGAAATCAATGAAGACCTCAATATAGCTGCTGT  420
GGCCTCCAACTTTGCCACCACAGATCTTGAGACTGACCTGTTCACCAACTGGGAGACCAT  480
GAATGTGATTAGCACTGACACAGAGCAGGTGAACACAGATGCTGACAGGGGCAAGCTGCC  540
TGGCAAAAAACTCCCCCCAGATGTCCTGAGGGAGCTGGAGGCCAATGCCAGAAGGGCTGG  600
TTGCACAAGAGGCTGCCTCATTTGCCTCTCCCACATTAAGTGCACCCCTAAGATGAAGAA  660
ATTTATCCCTGGCAGGTGCCACACTTATGAAGGTGAAAAGGAGTCTGCTCAGGGAGGGAT  720
TGGAGAGGCAATTGTTGATATCCCAGAGATTCCTGGCTTCAAGGATAAGGAGCCACTGGA  780
CCAGTTTATTGCTCAAGTGGACCTCTGTGCTGATTGCACCACTGGCTGTCTGAAGGGCCT  840
TGCCAATGTCCAGTGCTCTGACCTCCTGAAGAAGTGGCTTCCCCAGAGGTGTACCACTTT  900
TGCCAGCAAGATTCAGGGTAGGGTGGACAAAATCAAGGGTCTGGCTGGGGACAGATGAAG  960
CTAGCTGGCCAGACATGATAAGATACATTGATGAGTTTGGACAAACCACAACTAGAATGC 1020
AGTGAAAAAATGCTTTATTTGTGAAATTTGTGATGCTATTGCTTTATTTGTAACCATTA  1080
TAAGCTGCAATAAACAAGTTAACAACAACAATTGCATTCATTTTATGTTTCAGGTTCAGG 1140
GGGAGGTGTGGGAGGTTTTTTAAAGCAAGTAAAACCTCTACAAATGTGGTATG        1193
```

FIG. 9

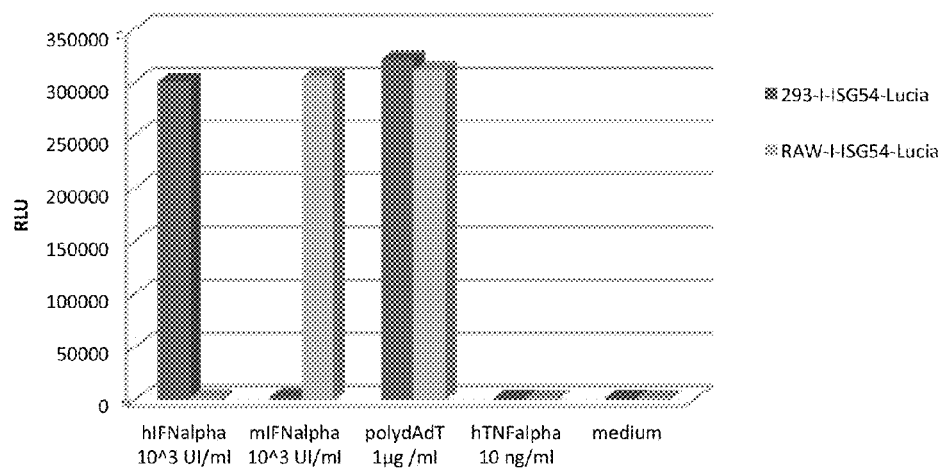

FIG. 10

SEQUENCE LISTING

```
<160> NUMBER OF SEQ ID NOS: 36

<210> SEQ ID NO 1
<211> LENGTH: 630
<212> TYPE: DNA
<213> ORGANISM: Artificial Sequence
<220> FEATURE:
<223> OTHER INFORMATION: CpG free gene SLuc

<400> SEQUENCE: 1
atggaaatca aggtgctgtt tgccctcatc tgtattgctg ttgctgaggc aaaacccact      60
gaaatcaatg aagacctcaa tatagctgct gtggcctcca actttgccac cacagatctt     120
gagactgacc tgttcaccaa ctgggagacc atgaatgtga ttagcactga cacagagcag     180
gtgaacacag atgctgacag gggcaagctg cctggcaaaa aactcccccc agatgtcctg     240
agggagctgg aggccaatgc cagaagggct ggttgcacaa gaggctgcct catttgcctc     300
tcccacatta agtgcacccc taagatgaag aaatttatcc ctggcaggtg ccacacttat     360
gaaggtgaaa aggagtctgc tcagggaggg attggagagg caattgttga tatcccagag     420
attcctggct tcaaggataa ggagccactg gaccagttta ttgctcaagt ggacctctgt     480
gctgattgca ccactggctg tctgaagggc cttgccaatg tccagtgctc tgacctcctg     540
aagaagtggc ttccccagag gtgtaccact tttgccagca agattcaggg tagggtggac     600
aaaatcaagg gtctggctgg ggacagatga                                      630

<210> SEQ ID NO 2
<211> LENGTH: 209
<212> TYPE: PRT
<213> ORGANISM: Artificial Sequence
<220> FEATURE:
<223> OTHER INFORMATION: Lucia pre-protein

<400> SEQUENCE: 2

Met Glu Ile Lys Val Leu Phe Ala Leu Ile Cys Ile Ala Val Ala Glu
1               5                   10                  15

Ala Lys Pro Thr Glu Ile Asn Glu Asp Leu Asn Ile Ala Ala Val Ala
                20                  25                  30

Ser Asn Phe Ala Thr Thr Asp Leu Glu Thr Asp Leu Phe Thr Asn Trp
            35                  40                  45
```

```
Glu Thr Met Asn Val Ile Ser Thr Asp Thr Glu Gln Val Asn Thr Asp
         50                  55                  60

Ala Asp Arg Gly Lys Leu Pro Gly Lys Lys Leu Pro Pro Asp Val Leu
 65                  70                  75                  80

Arg Glu Leu Glu Ala Asn Ala Arg Arg Ala Gly Cys Thr Arg Gly Cys
                 85                  90                  95

Leu Ile Cys Leu Ser His Ile Lys Cys Thr Pro Lys Met Lys Lys Phe
                100                 105                 110

Ile Pro Gly Arg Cys His Thr Tyr Glu Gly Glu Lys Glu Ser Ala Gln
            115                 120                 125

Gly Gly Ile Gly Glu Ala Ile Val Asp Ile Pro Glu Ile Pro Gly Phe
        130                 135                 140

Lys Asp Lys Glu Pro Leu Asp Gln Phe Ile Ala Gln Val Asp Leu Cys
145                 150                 155                 160

Ala Asp Cys Thr Thr Gly Cys Leu Lys Gly Leu Ala Asn Val Gln Cys
                165                 170                 175

Ser Asp Leu Leu Lys Lys Trp Leu Pro Gln Arg Cys Thr Thr Phe Ala
                180                 185                 190

Ser Lys Ile Gln Gly Arg Val Asp Lys Ile Lys Gly Leu Ala Gly Asp
            195                 200                 205

Arg
```

<210> SEQ ID NO 3
<211> LENGTH: 192
<212> TYPE: PRT
<213> ORGANISM: Artificial Sequence
<220> FEATURE:
<223> OTHER INFORMATION: Lucia protein

<400> SEQUENCE: 3

```
Lys Pro Thr Glu Ile Asn Glu Asp Leu Asn Ile Ala Ala Val Ala Ser
 1               5                  10                  15

Asn Phe Ala Thr Thr Asp Leu Glu Thr Asp Leu Phe Thr Asn Trp Glu
                 20                  25                  30

Thr Met Asn Val Ile Ser Thr Asp Thr Glu Gln Val Asn Thr Asp Ala
             35                  40                  45

Asp Arg Gly Lys Leu Pro Gly Lys Lys Leu Pro Pro Asp Val Leu Arg
 50                  55                  60

Glu Leu Glu Ala Asn Ala Arg Arg Ala Gly Cys Thr Arg Gly Cys Leu
 65                  70                  75                  80

Ile Cys Leu Ser His Ile Lys Cys Thr Pro Lys Met Lys Lys Phe Ile
                 85                  90                  95

Pro Gly Arg Cys His Thr Tyr Glu Gly Glu Lys Glu Ser Ala Gln Gly
            100                 105                 110

Gly Ile Gly Glu Ala Ile Val Asp Ile Pro Glu Ile Pro Gly Phe Lys
        115                 120                 125

Asp Lys Glu Pro Leu Asp Gln Phe Ile Ala Gln Val Asp Leu Cys Ala
130                 135                 140

Asp Cys Thr Thr Gly Cys Leu Lys Gly Leu Ala Asn Val Gln Cys Ser
145                 150                 155                 160

Asp Leu Leu Lys Lys Trp Leu Pro Gln Arg Cys Thr Thr Phe Ala Ser
                165                 170                 175

Lys Ile Gln Gly Arg Val Asp Lys Ile Lys Gly Leu Ala Gly Asp Arg
            180                 185                 190
```

<210> SEQ ID NO 4
<211> LENGTH: 561
<212> TYPE: DNA
<213> ORGANISM: Artificial Sequence
<220> FEATURE:
<223> OTHER INFORMATION: CpG free gene G-Luc

<400> SEQUENCE: 4

```
atgggagtca aggtgctgtt tgccctcatc tgtattgctg ttgctgaggc aaaacccact      60
gaaaacaatg aagacttcaa tatagttgct gtggcctcca actttgccac cacagacctt     120
gatgctgaca gggcaagct gcctggcaaa aaactccccc tagaagtcct gaaggagatg      180
gaggccaatg ccagaaaggc tggttgcaca agaggctgcc tcatttgcct ctcccacatt     240
aagtgcaccc ccaagatgaa gaaatttatc cctggcaggt gccacactta tgaaggtgac     300
aaggagtctg ctcagggagg gattggagag gcaattgttg atatcccaga gattcctggc     360
ttcaaggatt tggagccaat ggaacagttt attgctcaag tggacctctg tgtggattgc     420
accactggct gtctgaaggg ccttgccaat gtccagtgct ctgacctcct gaagaagtgg     480
cttccccaga ggtgtgccac ttttgccagc aagattcagg gtcaggtgga caaaatcaag     540
ggtgcaggtg gggactgatg a                                               561
```

<210> SEQ ID NO 5
<211> LENGTH: 630
<212> TYPE: DNA
<213> ORGANISM: Artificial Sequence
<220> FEATURE:
<223> OTHER INFORMATION: CPG free gene Mp-luc1

<400> SEQUENCE: 5

```
atggaaatcc aggtgctgtt tgccctcatc tgctttgccc tggtgcaggc caacccccact     60
gaaaacaagg atgacattga catagttggg gtggagggca gtttggcac cactgacctt      120
gagactgacc tgttcaccat tgtggaggac atgaatgtga ttagcaggga cacaaacctg     180
gccaactcag atgctgacag gggcaagatg cctggcaaaa actcccccct agaggtcctg     240
attgagatgg aggccaatgc cagaaaggct ggttgcacaa gaggctgcct catttgcctc     300
agcaagatta agtgcacagc caagatgaag gtctacatcc ctggcaggtg ccatgactat     360
gggggtgaca agaagactgg tcaggcaggg attgttgggg caattgttga tatcccagag     420
attagtggct tcaaggagct ggggccaatg gagcagtta ttgctcaagt ggacctctgt      480
gctgattgca ccactggctg tctgaagggc cttgccaatg tcaagtgctc tgccctcctg     540
aagaagtggc ttccagacag gtgtgcctct tttgctgaca gattcagtc tgaggtggac      600
aacatcaagg gtctggctgg ggacagatga                                      630
```

<210> SEQ ID NO 6
<211> LENGTH: 660
<212> TYPE: DNA
<213> ORGANISM: Artificial Sequence
<220> FEATURE:
<223> OTHER INFORMATION: CPG free gene Ml-luc

<400> SEQUENCE: 6

```
atggacatta aggtggtgtt caccctggtc ttctctgccc tggtgcaggc caagagcact      60
gaatttgacc ccaacattga catagttggc cttgagggca gtttgggat caccaacctg      120
gagacagacc tcttcaccat ctgggagacc atggaggtga tgatcaaggc tgacattgct     180
gacactgaca gggctagtaa cttttgtggcg acagagacag atgctaacag gggcaagatg     240
cctggcaaaa aactccccct agctgtcatc atggagatgg aggccaatgc cttcaaggct     300
```

```
ggttgcacaa gaggctgcct catttgcctc tccaagatta agtgcacagc caagatgaag    360
gtctacatcc ctggcaggtg ccatgactat gggggtgaca agaagactgg tcaggcaggg    420
attgtggggg caattgttga tatcccagag attagtggct tcaaggagat ggccccaatg    480
gagcagttta ttgctcaagt ggacaggtgt gcttcctgca ccactggctg tctgaagggc    540
cttgccaatg tcaagtgctc tgagctcctg aagaagtggc ttcctgacag gtgtgcctct    600
tttgctgaca agattcagaa ggaggtgcac aacatcaagg gtatggctgg ggacagatga    660
```

<210> SEQ ID NO 7
<211> LENGTH: 570
<212> TYPE: DNA
<213> ORGANISM: Artificial Sequence
<220> FEATURE:
<223> OTHER INFORMATION: CPG-free gene Mp-luc2

<400> SEQUENCE: 7

```
atgggagtca agctgatctt tgctgtggtc tgtgtggcag cagctcaggc agcaaccatc     60
aatgaaaact ttgaggacat tgacctggtt gccattggag ctccttttgc actggatgtt    120
gatgccaaca ggggaggtca tgggggccac cctggcaaaa aaatgcccaa agaggtcctg    180
gtggagatgg aggccaatgc caaaagggct ggttgccaca gaggctgcct catttgcctc    240
agccacatta agtgcaccaa gaagatgaag aaatttatcc ctggcaggtg ccactcttat    300
gaaggtgaca aggactctgc tcagggaggg attggagagg aaattgttga tatgccagag    360
attcctggct tcaaggataa ggagccaatg gaccagttta ttgctcaagt ggacctctgt    420
gtggattgca ccactggctg tctgaagggc cttgccaatg tccactgctc tgacctcctg    480
aagaagtggc ttcccagcag gtgtaagact tttgcctcca agattcagag tcaggtggac    540
acaatcaagg gtctggctgg ggacagatga                                     570
```

<210> SEQ ID NO 8
<211> LENGTH: 189
<212> TYPE: PRT
<213> ORGANISM: Artificial Sequence
<220> FEATURE:
<223> OTHER INFORMATION: Mp-luc2 pre-protein

<400> SEQUENCE: 8

```
Met Gly Val Lys Leu Ile Phe Ala Val Val Cys Val Ala Ala Ala Gln
  1               5                  10                  15

Ala Ala Thr Ile Asn Glu Asn Phe Glu Asp Ile Asp Leu Val Ala Ile
             20                  25                  30

Gly Gly Ser Phe Ala Leu Asp Val Asp Ala Asn Arg Gly Gly His Gly
         35                  40                  45

Gly His Pro Gly Lys Lys Met Pro Lys Glu Val Leu Val Glu Met Glu
     50                  55                  60

Ala Asn Ala Lys Arg Ala Gly Cys His Arg Gly Cys Leu Ile Cys Leu
 65                  70                  75                  80

Ser His Ile Lys Cys Thr Lys Lys Met Lys Lys Phe Ile Pro Gly Arg
                 85                  90                  95

Cys His Ser Tyr Glu Gly Asp Lys Asp Ser Ala Gln Gly Gly Ile Gly
            100                 105                 110

Glu Glu Ile Val Asp Met Pro Glu Ile Pro Gly Phe Lys Asp Lys Glu
        115                 120                 125

Pro Met Asp Gln Phe Ile Ala Gln Val Asp Leu Cys Val Asp Cys Thr
    130                 135                 140
```

```
Thr Gly Cys Leu Lys Gly Leu Ala Asn Val His Cys Ser Asp Leu Leu
145                 150                 155                 160

Lys Lys Trp Leu Pro Ser Arg Cys Lys Thr Phe Ala Ser Lys Ile Gln
                165                 170                 175

Ser Gln Val Asp Thr Ile Lys Gly Leu Ala Gly Asp Arg
            180                 185
```

<210> SEQ ID NO 9
<211> LENGTH: 185
<212> TYPE: PRT
<213> ORGANISM: Artificial Sequence
<220> FEATURE:
<223> OTHER INFORMATION: G-Luc pre-protein

<400> SEQUENCE: 9

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185
```

<210> SEQ ID NO 10
<211> LENGTH: 210
<212> TYPE: PRT
<213> ORGANISM: Artificial Sequence
<220> FEATURE:
<223> OTHER INFORMATION: Mp-luc1 pre-protein

<400> SEQUENCE: 10

```
Met Met Glu Ile Gln Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asn Leu Ala Asn Ser
50                  55                  60

Asp Ala Asp Arg Gly Lys Met Pro Gly Lys Lys Leu Pro Leu Glu Val
65                  70                  75                  80
```

```
Leu Ile Glu Met Glu Ala Asn Ala Arg Lys Ala Gly Cys Thr Arg Gly
            85                  90                  95

Cys Leu Ile Cys Leu Ser Lys Ile Lys Cys Thr Ala Lys Met Lys Val
            100                 105                 110

Tyr Ile Pro Gly Arg Cys His Asp Tyr Gly Gly Asp Lys Lys Thr Gly
            115                 120                 125

Gln Ala Gly Ile Val Gly Ala Ile Val Asp Ile Pro Glu Ile Ser Gly
            130                 135                 140

Phe Lys Glu Leu Gly Pro Met Glu Gln Phe Ile Ala Gln Val Asp Leu
145                 150                 155                 160

Cys Ala Asp Cys Thr Thr Gly Cys Leu Lys Gly Leu Ala Asn Val Lys
            165                 170                 175

Cys Ser Ala Leu Leu Lys Lys Trp Leu Pro Asp Arg Cys Ala Ser Phe
            180                 185                 190

Ala Asp Lys Ile Gln Ser Glu Val Asp Asn Ile Lys Gly Leu Ala Gly
            195                 200                 205

Asp Arg
    210

<210> SEQ ID NO 11
<211> LENGTH: 219
<212> TYPE: PRT
<213> ORGANISM: Artificial Sequence
<220> FEATURE:
<223> OTHER INFORMATION: M1-luc pre-protein

<400> SEQUENCE: 11

Met Asp Ile Lys Val Val Phe Thr Leu Val Phe Ser Ala Leu Val Gln
1               5                   10                  15

Ala Lys Ser Thr Glu Phe Asp Pro Asn Ile Asp Ile Val Gly Leu Glu
            20                  25                  30

Gly Lys Phe Gly Ile Thr Asn Leu Gly Thr Asp Leu Phe Thr Ile Trp
            35                  40                  45

Glu Thr Met Glu Val Met Ile Lys Ala Asp Ile Ala Asp Thr Asp Arg
50                  55                  60

Ala Ser Asn Phe Val Ala Thr Glu Thr Asp Ala Asn Arg Gly Lys Met
65                  70                  75                  80

Pro Gly Lys Lys Leu Pro Leu Ala Val Ile Met Glu Met Glu Ala Asn
            85                  90                  95

Ala Phe Lys Ala Gly Cys Thr Arg Gly Cys Leu Ile Cys Leu Ser Lys
            100                 105                 110

Ile Lys Cys Thr Ala Lys Met Lys Val Tyr Ile Pro Gly Arg Cys His
            115                 120                 125

Asp Tyr Gly Gly Asp Lys Lys Thr Gly Gln Ala Gly Ile Val Gly Ala
            130                 135                 140

Ile Val Asp Ile Pro Glu Ile Ser Gly Phe Lys Glu Met Ala Pro Met
145                 150                 155                 160

Glu Gln Phe Ile Ala Gln Val Asp Arg Cys Ala Ser Cys Thr Thr Gly
            165                 170                 175

Cys Leu Lys Gly Leu Ala Asn Val Lys Cys Ser Glu Leu Leu Lys Lys
            180                 185                 190

Trp Leu Pro Asp Arg Cys Ala Ser Phe Ala Asp Lys Ile Gln Lys Glu
            195                 200                 205

Val His Asn Ile Lys Gly Met Ala Gly Asp Arg
210                 215
```

<210> SEQ ID NO 12
<211> LENGTH: 1193
<212> TYPE: DNA
<213> ORGANISM: Artificial Sequence
<220> FEATURE:
<223> OTHER INFORMATION: CpG free expression cassette of Lucia

<400> SEQUENCE: 12

```
gctgaattag tttcactttc cagtttcagt ttccagtttc attttccagt ttcattttcc      60
agtttcattt tcctgatatc ctgcaggaaa aagagtcctc taaagtataa taaaaagaaa     120
aaaagaaaaa gagtcctgcc aatttcactt tctagtttca ctttcccttt tgtaatgtca     180
gctgaaggga aacaaacaaa aaggaaccag aggccacttg tatatatagg tctcttcagc     240
atttattggt ggcagaagag gaagatttct gaagagtgca gctgcctgaa ctgagccctg     300
ctgaacagct gagaattgca ctgcaaccat ggaaatcaag gtgctgtttg ccctcatctg     360
tattgctgtt gctgaggcaa acccactga aatcaatgaa gacctcaata tagctgctgt      420
ggcctccaac tttgccacca cagatcttga gactgacctg ttcaccaact gggagaccat     480
gaatgtgatt agcactgaca cagagcaggt gaacacagat gctgacaggg gcaagctgcc     540
tggcaaaaaa ctcccccccag atgtcctgag ggagctggag gccaatgcca aagggctgg      600
ttgcacaaga ggctgcctca tttgcctctc ccacattaag tgcaccccta agatgaagaa     660
atttatccct ggcaggtgcc acacttatga aggtgaaaag gagtctgctc agggagggat     720
tggagaggca attgttgata tcccagagat tcctggcttc aaggataagg agccactgga     780
ccagtttatt gctcaagtgg acctctgtgc tgattgcacc actggctgtc tgaagggcct     840
tgccaatgtc cagtgctctg acctcctgaa gaagtggctt ccccagaggt gtaccacttt     900
tgccagcaag attcaggta gggtggacaa aatcaagggt ctggctgggg acagatgaag      960
ctagctggcc agacatgata agatacattg atgagtttgg acaaaccaca actagaatgc    1020
agtgaaaaaa atgctttatt tgtgaaattt gtgatgctat tgctttattt gtaaccatta    1080
taagctgcaa taaacaagtt aacaacaaca attgcattca ttttatgttt caggttcagg    1140
gggaggtgtg ggaggttttt taaagcaagt aaaacctcta caaatgtggt atg           1193
```

<210> SEQ ID NO 13
<211> LENGTH: 558
<212> TYPE: DNA
<213> ORGANISM: Artificial Sequence
<220> FEATURE:
<223> OTHER INFORMATION: humanized G-luc

<400> SEQUENCE: 13

```
atgggagtca agttctgtt tgccctgatc tgcatcgctg tggccgaggc caagcccacc       60
gagaacaacg aagacttcaa catcgtggcc gtggccagca cttcgcgac cacggatctc     120
gatgctgacc gcgggaagtt gcccggcaag aagctgccgc tggaggtgct caaagagatg    180
gaagccaatg cccggaaagc tggctgcacc agggggctgtt tgatctgcct gtcccacatc    240
aagtgcacgc ccaagatgaa gaagttcatc ccaggacgct gccacaccta cgaaggcgac    300
aaaagagtccg cacagggcgg catagggcgag gcgatcgtcg acattcctga gattcctggg    360
ttcaaggact ggagcctat ggagcagttc atcgcacagg tcgatctgtg tgtggactgc     420
acaactggct gcctcaaagg gcttgccaac gtgcagtgtt ctgacctgct caagaagtgg    480
ctgccgcaac gctgtgcgac ctttgccagc aagatccagg gccaggtgga caagatcaag    540
ggggccggtg gtgactaa                                                   558
```

```
<210> SEQ ID NO 14
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 14
acagtagctt ccaccatgga antcnagntg                                30

<210> SEQ ID NO 15
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
```

<222> LOCATION: (58)..(58)
<223> OTHER INFORMATION: n is a, c, g, or t

<400> SEQUENCE: 15
ntgtttgccn tcntctgtnt tgctnttnct naggcanaan ccactgaant cnatnaanac    60

<210> SEQ ID NO 16
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 16
ntcnatatag ttnctntgnc cnccnacttt nccaccacan atcttgagnc tnacctgttc    60

<210> SEQ ID NO 17
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 17
accatcnggg agnccatgna tgtgattagc agtgacacan agntgntgna cncagatgct      60

<210> SEQ ID NO 18
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 18
nacaggggcn agntgcctgg caaaaaactc cccntanatg tcntgntgga gntggaggcc      60

<210> SEQ ID NO 19
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t

<400> SEQUENCE: 19
aatgccngan gggctggttg cncaagaggc tgcctcattt gcctcnccna cattaagtgc      60

<210> SEQ ID NO 20
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 20
accnctaaga tgaagnaant tatccctggc aggtgccacn cttatnaagg tgacaagnag      60

<210> SEQ ID NO 21
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
```

<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t

<400> SEQUENCE: 21
nctnctcagn gagggattng anaggcaatt gttgatatcc cagagattnc tggcttcaag    60

<210> SEQ ID NO 22
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t

<400> SEQUENCE: 22
natnagnagc cantgnacca gtttattgct caagtggacn tctgtnctna ttgcaccact    60

<210> SEQ ID NO 23
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 23
ggctgtctga agggccttgc caatgtcnag tgctctnacc tcctgaagaa gtggcttccc    60

```
<210> SEQ ID NO 24
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 24
nagaggtgtn ccncttttgc cngcaagatt cagngtnagg tgnacnaaat caagggtntg    60

<210> SEQ ID NO 25
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 25
nctggggacn gatgatagct agctggccag                                     30

<210> SEQ ID NO 26
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
```

<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 26
agnaanagca anacaganga nggcaaacan canctngant tccatggtgg aagctactgt    60

<210> SEQ ID NO 27
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature

```
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 27
aaagtnggng gncanagnaa ctatatngan gtntnatng anttcagtgg nttntgcctn      60

<210> SEQ ID NO 28
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 28
gctaatcaca tncatggnct cccngatggt gaacaggtna gnctcaagat ntgtggtggn      60

<210> SEQ ID NO 29
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
```

<222> LOCATION: (30)..(30)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 29
gagttttttg ccaggcanct ngcccctgtn agcatctgng tncancanct ntgtgtcact     60

<210> SEQ ID NO 30
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 30
gcctcttgng caaccagccc ntcnggcatt ggcctccanc tccancanga catntanggg     60

<210> SEQ ID NO 31
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 31
gccagggata anttncttca tcttagnggt gcacttaatg tnggngaggc aaatgaggca      60

<210> SEQ ID NO 32
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 32
aattgcctnt cnaatccctc nctgagnagn ctncttgtca ccttnataag ngtggcacct      60

<210> SEQ ID NO 33
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
```

```
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 33
agcaataaac tggtncantg gctnctnatn cttgaagcca gnaatctctg ggatatcaac    60

<210> SEQ ID NO 34
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 34
ctngacattg gcaaggccct tcagacagcc agtggtgcaa tnagnacaga ngtccacttg    60

<210> SEQ ID NO 35
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 35
```

```
aatcttgcng gcaaaagngg nacacctctn gggaagccac ttcttcagga ggtnagagca    60

<210> SEQ ID NO 36
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 36
ctggccagct agctatcatc ngtccccagn canaccttg atttngtnca cctnacnctg    60
```

CPG-FREE GENE FOR A NEW SECRETED REPORTER PROTEIN

FIELD OF THE INVENTION

The present invention relates to isolated nucleic acid molecules encoding secreted proteins and luciferase proteins.

BACKGROUND OF THE INVENTION

Luciferases encompass a wide range of enzymes that catalyze bioluminescence reactions. Bioluminescence is the emission of light produced in a biochemical reaction involving the oxidation of a substrate via an enzyme that occurs within a living organism. Luciferases have been used extensively in different formats for life science research and drug discovery because they are non-toxic, highly sensitive and provide quantitative readouts. Examples of bioluminescence applications include gene reporter assays, whole-cell biosensor measurements, protein-protein interaction studies using bioluminescence resonance energy transfer (BRET), in vivo imaging and drug discovery through high throughput screening (De and Gambhir 2005; Fan and Wood 2007; Ray and Gambhir 2007; Yagi 2007; Sadikot and Blackwell 2008; Prescher and Contag 2010). A number of luciferases have been identified, varying according to their origin, enzyme activity and by their substrate specificity. Of the several luciferases that have been cloned and expressed in bacteria and/or mammalian cells, secreted luciferases have the advantageous characteristic in that their activity can be directly detected in the cell media without disrupting cells (Thompson et al. 1990; Inouye et al. 1992; Maguire et al. 2009; Griesenbach et al. 2011).

Origins of Luciferases

Luciferases are commonly found in lower organisms such as bacteria, fungi, insects, and marine crustaceans. The best-studied luciferases to date are the non-secreted forms of luciferases, such as the firefly luciferase (FLuc) found in the light-emitting organ of the firefly *Photinus pyralis* (de Wet et al. 1985) and *Renilla* luciferase (RLuc) from the sea pansy *Renilla reniformis* (Lorenz et al. 1991). While FLuc and RLuc are widely used as reporters in cultured cells, the major drawback with these non-secreted forms is that they are unsuitable for use in live cells since cell lysis is required prior to measurement of bioluminescence. Less well studied are the naturally secreted forms of luciferases from marine bioluminescent organisms, which carry advantages over non-secreted luciferases for use as reporters to continuously monitor gene expression in live cell-based assays. The secreted luciferase proteins contain signal sequences at their amino-termini targeting the release of the luciferase from the cytosol within the cell to the surrounding culture medium, when expressed either as the wild-type or as a recombinant form in mammalian cells. Thus, genes of secreted luciferases have been exploited for the design of reporter genes, monitoring gene expression in a sample of culture medium without disrupting cells. The first secreted luciferases cloned were *Vargula* and *Cypridina* luciferases, isolated from the marine ostracod crustaceans, *Vargula hilgendorfi* (Thompson et al. 1989) and *Cypridina noctiluca* (Nakajima et al. 2004), respectively. Their expression in mammalian cells has demonstrated their advantages as secreted reporters for monitoring gene expression in live cells (Inouye et al. 1992; Thompson et al. 1995). Secreted luciferases have since been isolated from the marine copepod crustaceans, *Gaussia* luciferase (GLuc) from *Gaussia princeps* (Verhaegent and Christopoulos 2002) and *Metridia longa* luciferase (MLuc) from *Metridia longa* (Markova et al. 2004, Golz et al. 2002. Pat. WO 02/42470). Two forms of secreted luciferases, MpLuc1 and MpLuc2, were isolated from another marine copepod *Metridia pacifica* (Takenaka et al. 2008; Takenaka 2009. U.S. Pat. No. 0,233, 320 A1). More recently, in a filed patent (Golz et al. US Pat. No. 2010/0105090), a new secreted luciferase from *Metridia longa*, named MLuc7 has been described.

Table of Luciferases

| Name | Species | Form | Substrate | Kinetics |
|------|---------|------|-----------|----------|
| FLuc | *Photinus pyralis* (Firefly) | Non-secreted | D-Luciferin | Glow |
| RLuc | *Renilla reniformis* | Non-secreted | Coelenterazine | Flash |
| Vargula | *Vargula hilgendorfi* | Secreted | Luciferin | Glow |
| Cypridina | *Cypridina noctiluca* | Secreted | Luciferin | Glow |
| GLuc | *Gaussia princeps* | Secreted | Coelenterazine | Flash |
| MLuc/MLuc7 | *Metridia longa* | Secreted | Coelenterazine | Flash |
| MpLuc1/MpLuc2 | *Metridia pacifica* | Secreted | Coelenterazine | Flash |

Substrates of Luciferases and Enzyme Properties

Substrates of luciferases can be broadly classed into two groups; derivatives of luciferin and coelenterazine. Luciferases using luciferins as substrates require ATP and $Mg^{2+}$ as cofactors and display stable glow kinetics, whereas luciferases using coelenterazine do not require ATP for activity and, contrary to stable glow kinetics, display rapid flash kinetics. FLuc uses D-luciferin as a substrate and the oxidation reaction emits light with a peak wavelength of 562 nm (de Wet et al. 1985). RLuc uses coelenterazine as a substrate, emitting light with a peak at 480 nm (Lorenz et al. 1991). Although the slightly blue shifted light emission by luciferases that utilize coelenterazine as a substrate is less favorable for their application in in vivo bio-imaging, successful bio-imaging has been described due to their strong bioluminescence signal (De and Gambhir 2005; Griesenbach et al. 2011; Tannous and Teng 2011).

Of the secreted luciferases, *Vargula* and *Cypridina* luciferases are similar in size (62 kDa) and display similar enzymatic properties, using *Cypridina* luciferin as a substrate to produce blue light at a wavelength of 465 nm, oxyluciferin and carbon dioxide. However the secreted luciferases isolated from the marine copepod crustaceans, *Gaussia* luciferase and *Metridia longa* luciferase, are considerably smaller proteins employing substrate specificity toward coelenterazine (Verhaegent and Christopoulos 2002; Markova et al. 2004). *Gaussia* luciferase contains only 185 amino acids (19.9 kDa) while *Metridia longa* luciferase is a 219-amino acid polypeptide (23.9 kDa). From *Metridia pacfica*, MpLuc1 consists of 210 amino acids (22.7 kDa) and has the closest homology with *Metridia longa* luciferase while MpLuc2 (Takenaka et al. 2008) which comprises 189 amino acids (20.3 kDa), has the closest homology with *Gaussia* luciferase. The recently identified MLuc7 is the smallest luciferase currently known at 169 amino acids (18.4 kDa) (Golz et al. US Pat. No. 2010/0105090).

Similar to the non-secreted RLuc, secreted luciferases from marine copepods catalyze the oxidation of coelenterazine to coelenteramide to produce light at a wavelength of 475 nm, independent of any co-factor (Markova et al. 2004). In summary, distinct properties of the copecod luciferases, primarily the fact that they are secreted and that they display stronger bioluminescence signal render advantages for their use in reporter studies over other luciferases such as FLuc and RLuc (Haugwitz et al. 2008). Furthermore, mutations of secreted luciferases have been described to improved properties such as enhanced light stability and red-shifted emission (Tannous et al. 2005; Haugwitz et al. 2008; Maguire et al. 2009; Welsh et al. 2009; Kim et al. 2011; Tannous and Teng 2011; Tannous et al. 2011, Pat. WO 2011/002924, Kim et al. 2010, Pat. WO 2010/119721).

Applications of Secreted Luciferases

*Gaussia* luciferase, GLuc, is currently the most exploited secreted luciferase. GLuc cDNA was cloned and overexpressed in a bacterial system, and the protein was purified and used as a sensitive analytical reporter for hybridization assays in vitro (Bryan et al. 2001, U.S. Pat. No. 6,232,107; Verhaegent and Christopoulos 2002). GLuc has also been used for studying a variety of biological processes including quantification of tumor growth (Chung et al. 2009) and monitoring of microbial infections (Enjalbert et al. 2009), as well as in screening for small interfering (si)RNA (Lwa et al. 2010). GLuc is a thermostable, pH resistant protein and in vitro studies have shown that GLuc has more activity than other secreted luciferases as well as the secreted alkaline phosphatase, a commonly used secreted reporter in mammalian cells (Haugwitz et al. 2008). The GLuc cDNA, which consists of 555 by has been humanized by codon optimization for mammalian cell expression. The humanized, codon optimized version of GLuc (hGLuc) was shown to be highly expressed in mammalian cells compared to its wild-type form and to give orders of magnitude stronger bioluminescent signal compared to humanized forms of FLuc and RLuc (Tannous et al. 2005; Maguire et al. 2009). In addition, mutants of GLuc have demonstrated enhanced light stability and red-shifted emission (Maguire et al. 2009; Welsh et al. 2009; Tannous et al. 2011, Pat. WO 2011/002924, Kim et al. 2010, Pat. WO 2010/119721).

In many in vitro and in vivo biological applications, strong and sustained recombinant expression of reporter genes is essential. For instance, reporter genes are playing an increasingly important role in cancer gene therapy as a model transgene, where the aim is to achieve the sustained expression of a variety of anti-tumor proteins such as tumor-suppressor proteins, antigens, cytokines and suicide proteins. The expression stability of a transgene and the protein abundance depends on the nature of the expression cassette. Typically, a codon-optimized gene is combined with a strong viral promoter for enhanced and long-lasting expression. However, such optimized expression cassettes are subject to downregulation of gene expression via transcriptional silencing in vitro and in vivo.

There is a need for a new gene encoding secreted luciferase that displays higher and prolonged gene expression, and generates a secreted luciferase that displays stronger luciferase activity compared to that generated by a codon-optimized luciferase gene such as hGLuc gene.

SUMMARY OF THE INVENTION

The present invention relates to an isolated nucleic acid molecule encoding a preprotein comprising a signal peptide and a protein having luciferase activity and wherein said nucleic acid molecule is devoid of CpG.

The present invention also relates to an isolated protein having luciferase activity and having the amino acid sequence set forth as SEQ ID NO: 3.

The present invention also relates to an expression vector comprising the nucleic acid molecule of the invention operatively linked to a promoter.

The present invention also relates to a cell comprising the nucleic acid molecule of the invention or the expression vector comprising the nucleic acid molecule of the invention.

The present invention also relates to a kit comprising:
the nucleic acid molecule of the invention, an expression vector comprising the nucleic acid molecule of the invention or a cell comprising the nucleic acid molecule of the invention or an expression vector comprising the nucleic acid molecule of the invention and
a substrate of the protein having luciferase activity encoded by nucleic acid molecule of the invention.

The present invention also relates to method for detecting a molecule in a sample comprising the step of:
providing cell(s) having an expression vector comprising the nucleic acid molecule of the invention operatively linked to a promoter that is inducible by the molecule to be detected,
contacting said cell(s) with the sample,
measuring the luciferase activity in the sample.

DETAILED DESCRIPTION OF THE INVENTION

Unless defined otherwise, all technical and scientific terms used herein have the same meaning as is commonly understood by one of skill in the art to which this invention belongs.

As used herein, a cytosine monophosphate (C) followed by a guanine monophosphate (G) in a nucleic acid refers to as CpG dinucleotide.

The epigenetic modification of DNA, in particular methylation of CpG dinucleotides, plays an important role in the regulation of gene expression in eukaryotes (Tilghman 1999; Barlow 2010).

In eukaryotic DNA, CpG dinucleotides appear at a disproportionately low frequency according to their statistical expectation whereas in most bacterial genomes CpG dinucleotides are represented as expected. Eukaryotic DNA methylation affects only cytosine residues and specifically in a CpG dinucleotide motif by enzymes known as DNA methyltransferases. Three active DNA methyltransferases have been identified in mammals, named DNMT1, DNMT3A, and DNMT3B (Girault et al. 2003). These enzymes catalyze the methyl group transfer from S-adenosyl methionine to the 5' position of the pyrimidine ring of cytosine generating 5-methyl-cytosine (mCpG). While in bacteria, the cytosine residue is normally unmethylated, methylation of CpG dinucleotides in eukaryotes essentially serves to silence gene expression through interfering with the transcriptional machinery. CpG sites are commonly concentrated within regions termed CpG islands (CGIs), distributed throughout the genome but often rich within promoter regions (Esteller 2008). After DNA methylation, a common mechanism of gene silencing is through the binding of methylated DNA-binding proteins that subsequently recruit repressive complexes such as histone deacetylases (HDACs) (Marks et al. 2001). Histone deacetylation, induced by HDACs in the vicinity of promoter regions, leads to a chromatin compaction that in turn provokes a transcriptional repression of the gene.

Methylated CpGs repress transcription without significant influence from the surrounding sequence. The inactive X chromosome in females is a classic example of where promoter methylation correlates with the silencing of these genes (Pfeifer et al. 1990; Frommer et al. 1992). The epigenetic process of DNA methylation not only plays critical roles in differentiation and development, but also a significant role in disease. Whereas most CpG-islands remain unmethylated during normal development, aberrant hypermethylation is a hallmark of cancer resulting in silencing of tumor suppressor genes.

Nucleic acid molecules devoid of CpG may be, but are not limited to, genes, vectors or promoters or other nucleic acid molecules.

The human innate immune system has evolved DNA methylation as a mechanism to differentiate foreign DNA from its own. Bacterial CpG dinucleotides have been identified to be major contributors to the low and short-lived transgene expression in vertebrates after non-viral gene delivery. Studies have shown that foreign promoters in plasmid DNA, such as the strong and commonly used immediate-early gene promoter from cytomegalovirus, are prone to inactivation due to CpG methylation in contrast to those derived from housekeeping genes, leading to decreased expression (Graessmann et al. 1994; Prosch et al. 1996; Brooks et al. 2004; Bergbauer et al. 2011). Gene transfer studies in vivo of plasmid DNA with reduced CpG content by hydrodynamic injection, has been demonstrated to stabilize transgene expression (Hodges et al. 2004; Mitsui et al. 2009). In addition, pre-clinical and clinical studies have shown that non-viral gene transfer can provoke a mild, acute inflammatory response, partly due to unmethylated CpG dinucleotides present in the plasmid DNA (Yew et al. 2002; Hodges et al. 2004; Mitsui et al. 2009). Retention of even a single CpG in plasmid DNA is sufficient to elicit an inflammatory response (Hyde et al. 2008). CpG motifs within the gene transcribing unit as well as those residing within the plasmid DNA are recognized as a pathogen-associated molecular pattern upon entry into the cell, by toll-like receptors (Krieg et al. 1995; Medzhitov 2001).

The expression "devoid of CpG" or "CpG free" referred to a nucleic acid molecule having no CpG in its nucleic acid sequence.

Thus, because of the immunostimulatory effects in addition to the gene silencing evoked by methylation of CpG motifs, the use of CpG-free genes and vectors are crucial in gene transfer strategies where high and long lasting transgene levels are desired.

Several in vitro studies in cultured cells have as well clearly demonstrated a correlation between promoter methylation and gene repression. To counteract the limitation of CpG induced gene repression, plasmid DNA vectors completely devoid of CpGs have been generated (Drocourt et al. 2007, U.S. Pat. No. 7,244,609). The inventors have demonstrated that among the sixteen dinucleotides possible by the four DNA nucleotides, the CpG dinucleotide can be entirely avoided in DNA such as in bacterial plasmids and still remain fully functional. In addition, due to the degeneracy of the genetic code, it is theoretically possible to have genes entirely deprived of CpG. Indeed, CpG-free genes can be found in bacteria and in mammals, mostly among short genes, but with an extremely low frequency. Because of the ease to chemically synthesize large fragments of DNA, any gene can now be synthesized free of CpG although at the expense of a slightly reduced activity. Therefore, in addition to CpGs depletion in the promoter region of genes to stabilized gene expression, there are reports showing that the depletion of CpGs in the gene-transcribing unit significantly stabilizes expression (Chevalier-Mariette et al. 2003; Dalle et al. 2005). However, the depletion of CpG in the coding sequence may not always be sufficient for sustaining transgene expression, as indicated by a report where a CpG depleted reporter gene was associated with a reduction in protein expression (Bauer et al. 2010). Thus, multiple parameters that affect gene expression need to be taken into account (Mutskov and Felsenfeld 2004; Chodavarapu et al. 2011; Fath et al. 2011).

As used herein, a luciferase refers to an enzyme that catalyzes a bioluminescent reaction that produces bioluminescence.

As used herein, vector (or plasmid) refers to discrete elements that are used to introduce heterologous DNA into cells for either expression or replication thereof. Selection and use of such vehicles are well-known to those of skill in the art. An expression vector includes vectors capable of expressing DNAs that are operatively linked with regulatory sequences, such as promoters, that are capable of effecting expression of such DNA fragments. Thus, an expression vector refers to a recombinant DNA construct, such as a plasmid, a phage, recombinant virus or other vector that, upon introduction into an appropriate host cell, results in expression of the cloned DNA. Appropriate expression vectors are well known to those of skill in the art.

As used herein, a promoter refers to a segment of DNA that controls transcription of the DNA to which it is operatively linked.

As used herein, operatively linked refers to the functional relationship of DNA with regulatory and effector sequences of nucleotides, such as promoters, enhancers, transcriptional and translational stop sites, and other signal sequences.

For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

Reporter gene refers generally to genes whose genes products can be detected readily with the aid of simple biochemical or histochemical method.

As used herein, the percentage of sequence identity refers to comparisons among amino acid sequences, and is determined by comparing two optimally aligned sequences over a comparison window, wherein the portion of the amino acid sequence in the comparison window may comprise additions or deletions (i.e. gaps) as compared to the reference sequence (which does not comprise additions or deletions) for optimal alignment of the two sequences. The percentage may be calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical amino acid residue occurs in both sequences or an amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences.

Isolated Nucleic Acid Molecules of the Invention

The present invention relates to an isolated nucleic acid molecule encoding a preprotein comprising a signal peptide and a protein having luciferase activity and wherein said nucleic acid molecule is devoid of CpG. Indeed, the The preprotein encoded by nucleic acid molecule of the invention contains a signal sequence at the amino-terminus, thus when expressed in a cell, particularly a mammalian cell, is released from the cytosol within the cell to the surrounding culture medium.

Hereinafter, proteins having luciferase activity that, when expressed, are released by the host cell from the cytosol into the surrounding medium are referred to as secreted luciferases.

Thus, the protein of the invention is typically a secreted luciferase.

Contrary to the other known nucleic acid molecules coding for secreted luciferases, the nucleic acid molecule according the invention is devoid of CpG. Thus, the expression of this nucleic acid molecule is stable in mammalian cells. Further to the higher and prolonged expression of the molecule, it generates a secreted luciferase that displays stronger luciferase activity.

The ability to be secreted of the luciferase according to the makes it a particularly useful reporter. It can be easily measured for example in a culture medium without lysing the cells contrary to non-secreted luciferases.

The advantages of secreted luciferases as secreted reporters for real-time ex vivo monitoring of in vivo biological processes have recently been reviewed by Tannous et al. (Tannous and Teng 2011).

In a preferred embodiment, the isolated nucleic acid molecule of the invention has the nucleic acid sequence set forth as SEQ ID NO:1.

The inventors have found that the isolated nucleic acid molecule is particularly relevant both in term of stability of expression and in term of activity of the expressed and secreted luciferase.

The isolated nucleic acid molecule of the invention having the nucleic acid sequence set forth as SEQ ID NO:1 corresponds to a gene called SLuc hereinafter.

In a preferred embodiment, the preprotein encoded by the isolated nucleic acid molecule of the invention has the amino acid sequence set forth as SEQ ID NO: 2.

The preprotein of the invention having the amino acid sequence set forth as SEQ ID NO: 2 corresponds to a preprotein comprising a signal peptide and a mature secreted protein with luciferase activity.

In a preferred embodiment, the protein having luciferase activity comprised in the preportein encoded by the isolated nucleic acid molecule of the invention has the amino acid sequence set forth as SEQ ID NO: 3.

The mature secreted luciferase having the amino acid sequence set forth as SEQ ID NO: 3 is also called Lucia hereinafter.

In a preferred embodiment, the protein having luciferase activity comprised in the preportein encoded by the isolated nucleic acid molecule of the invention is a variant of the protein having the amino acid sequence set forth as SEQ ID NO: 3, which has a luciferase activity and contains more than 5 consecutive amino acids which are immunologically recognized by antibody directed against the protein having the amino acid sequence set forth as SEQ ID NO: 3.

Typically, the secreted luciferase of the invention has more than 5, 6, 7, 8, 9, 10, 15, 20, 25, 50, 75, 100, 125 or 150 consecutive amino acids which are immunologically recognized by antibody directed against the protein having the amino acid sequence set forth as SEQ ID NO: 3.

In a preferred embodiment, the activity of the secreted protein having luciferase activity encoded by the nucleic acid molecule of the invention is higher than the activity of the protein having luciferase activity encoded by the nucleic acid sequence of humanized GLuc (from Prolume or New England Biolabs), when the nucleic acid molecules are inserted in a expression vector and expressed in a mammalian cell line. The activities of theses proteins are measured in the cell culture media.

Protein of the Invention

The present invention relates to an isolated protein having luciferase activity being the preprotein encoded by the isolated nucleic acid molecule according to the invention from which the signal peptide has been removed.

The present invention also relates to an isolated protein having luciferase activity and having the amino acid sequence set forth as SEQ ID NO: 3.

Typically, the protein of the invention is a secreted luciferase.

The luciferase of the invention is with enhanced bioluminescence signal providing improved sensitivity and ease of use that can ultimately be applied to high-throughput techniques to quantitatively assay many samples robustly.

The present invention also relates to an isolated protein having luciferase activity and being a variant of the protein having the amino acid sequence set forth as SEQ ID NO: 3, which contains more than 5 consecutive amino acids which are immunologically recognized by antibody directed against the protein having the amino acid sequence set forth as SEQ ID NO: 3.

In one embodiment, the protein of the invention has luciferase activity and is selected from the group consisting of the protein with the amino acid sequence of SEQ ID NO:3 or proteins with amino acid sequence having at least 95% identity with SEQ ID NO:3. Indeed, the amino acid sequence of the luciferase according to the invention may be modified, e.g. by substitution, deletion or addition of 1, 2, 3, 4, 5, 6, 7, 8, 9, 10, 11, 12, 13, 14 or 15 amino acids as compared to the native sequence SEQ ID NO:3.

The luciferases according to the invention are thus proteins having luciferase activity and having amino acid sequence of SEQ ID NO:3 or amino acid sequences having at least 95%, 96%, 97%, 98%, or at least 99% identity with SEQ ID NO:3.

Expression Vector of the Invention

The invention also relates to an expression vector comprising the nucleic acid molecule according to the invention operatively linked to a promoter.

The nucleic acid molecule may be used as a reporter gene in assays to study a variety of biological events. By placing the nucleic acid molecule of the invention under control of a specific promoter, when activated downstream of a particular signaling pathway, it results in expression of the luciferase protein.

In a preferred embodiment, the promoter of expression vector is devoid of CpG.

Plasmid DNA vectors completely devoid of CpGs have been described (Drocourt et al. 2007, U.S. Pat. No. 7,244, 609).

In a preferred embodiment, the promoter is an interferon inducible promoter.

Interferon inducible promoters are well-known in the art and many interferon inducible promoters are commercially available.

The promoter may be the promoter inducible by an alpha interferon, a beta interferon or a lambda interferon.

The promoter may be an IL28 inducible promoter.

Cell of the Invention

The present invention also relates to a cell comprising the nucleic acid molecule of the invention or the expression vector comprising the nucleic acid molecule of the invention.

Thus, the nucleic acid molecule according to the invention may be used as a reporter gene in live cell-based assays to study a variety of biological events.

For example, the nucleic acid of the invention may be placed under control of a specific promoter that when activated downstream of a particular signalling pathway, results in expression of the luciferase and its secretion from cells into the culture media. Bioluminescence assays for luciferase activity are conducted directly from culture media containing secreted luciferase of the invention, providing a readout of the biological signalling event under study. The advantages of secreted luciferases as secreted reporters for real-time ex vivo monitoring of in vivo biological processes have recently been reviewed by Tannous et al. (Tannous and Teng 2011).

The inventors have demonstrated improvements over existing in vitro live cell-based reporter assays.

Indeed, the secreted luciferase encoded by the nucleic acid molecule of the invention exhibits improved properties to evaluate transcriptional regulation associated with signaling pathways that are dysregulated in many human disorders including inflammation and cancer. Advantages of using the present invention include in particular more stable expression of the transgene in cell culture. Furthermore the nucleic acid molecule of the invention encodes for a luciferase with enhanced bioluminescence signal providing improved sensitivity and ease of use that can ultimately be applied to high-throughput techniques to quantitatively assay many samples robustly.

In one embodiment, the cell according the invention comprises a further reporter gene.

Thus, two distinct pathways may be assayed in the same live cell-based assay. Preferably, the further reporter gene is devoid of CpG.

The further reporter gene may be a secreted embryonic alkaline phosphatase (SEAP) reporter gene and more preferably a secreted embryonic alkaline phosphatase (SEAP) reporter gene devoid of CpG.

Kit of the Invention

The present invention also relates to a kit comprising the nucleic acid molecule according to the invention, an expression vector comprising the nucleic acid molecule according to the invention or a cell comprising the nucleic acid molecule according to the invention or an expression vector comprising the nucleic acid molecule according to the invention and a substrate of the protein having luciferase activity encoded by nucleic acid molecule according to the invention.

In a preferred embodiment, the nucleic acid molecule has the nucleic acid sequence set forth as SEQ ID NO:1.

In a preferred embodiment, the substrate of the protein having luciferase activity is coelenterazine.

Method of the Invention

The present invention also relates to a method for detecting a molecule in a sample comprising the step of:
  providing cell(s) having an expression vector comprising the nucleic acid molecule according to claim 1 operatively linked to a promoter which is inducible by the molecule to be detected,
  contacting said cell(s) with the sample,
  measuring the luciferase activity in the sample.

In one embodiment, the luciferase activity is measured by measuring the bioluminescence quantification of the cell culture media or a sample of the cell culture media.

The invention will be further illustrated by the following figures and examples. However, these examples and figures should not be interpreted in any way as limiting the scope of the present invention.

FIGURES

FIG. 1 shows nucleotide alignments of the Luciferase genes of the Copepod organisms.

Nucleic acid sequences of CpG-free G-luc wherein one codon STOP has been added, CpG-free Mp-luc1, CpG-free Ml-luc and CpG-free Mp-luc2 are respectively set forth as SEQ ID NO: 4, SEQ ID NO: 5, SEQ ID NO: 6 and SEQ ID NO: 7.

FIG. 2 shows nucleotide sequences of degenerate primers for the synthesis of CpG free luciferase variants (sense strand: odd oligos; reverse strand: even oligos).

FIG. 3 shows DNA sequence of the CpG-free Lucia gene, SLuc, SEQ ID NO: 1.

FIG. 4 shows amino-acid sequence of the pre-protein Lucia, SEQ ID NO: 2.

FIG. 5 shows amino-acid alignments of the Luciferases pre-proteins.

Amino acid sequences of Lucia, Mp-luc2, G-luc, Mp-luc1 and M[1]-luc are respectively set forth as SEQ ID NO: 2, SEQ ID NO: 8, SEQ ID NO: 9, SEQ ID NO: 10 and SEQ ID NO: 11.

FIG. 6 shows amino-acid sequence of the mature secreted protein Lucia SEQ ID NO: 3.

FIG. 7 shows nucleotide alignments of the CpG-free SLuc, CpG-free G-luc and hGLuc Luciferase genes.

Nucleic acid sequences of CpG-free SLuc, CpG-free G-luc and hGLuc are respectively set forth as SEQ ID NO: 1, SEQ ID NO: 4 and SEQ ID NO: 13.

Figure 8:
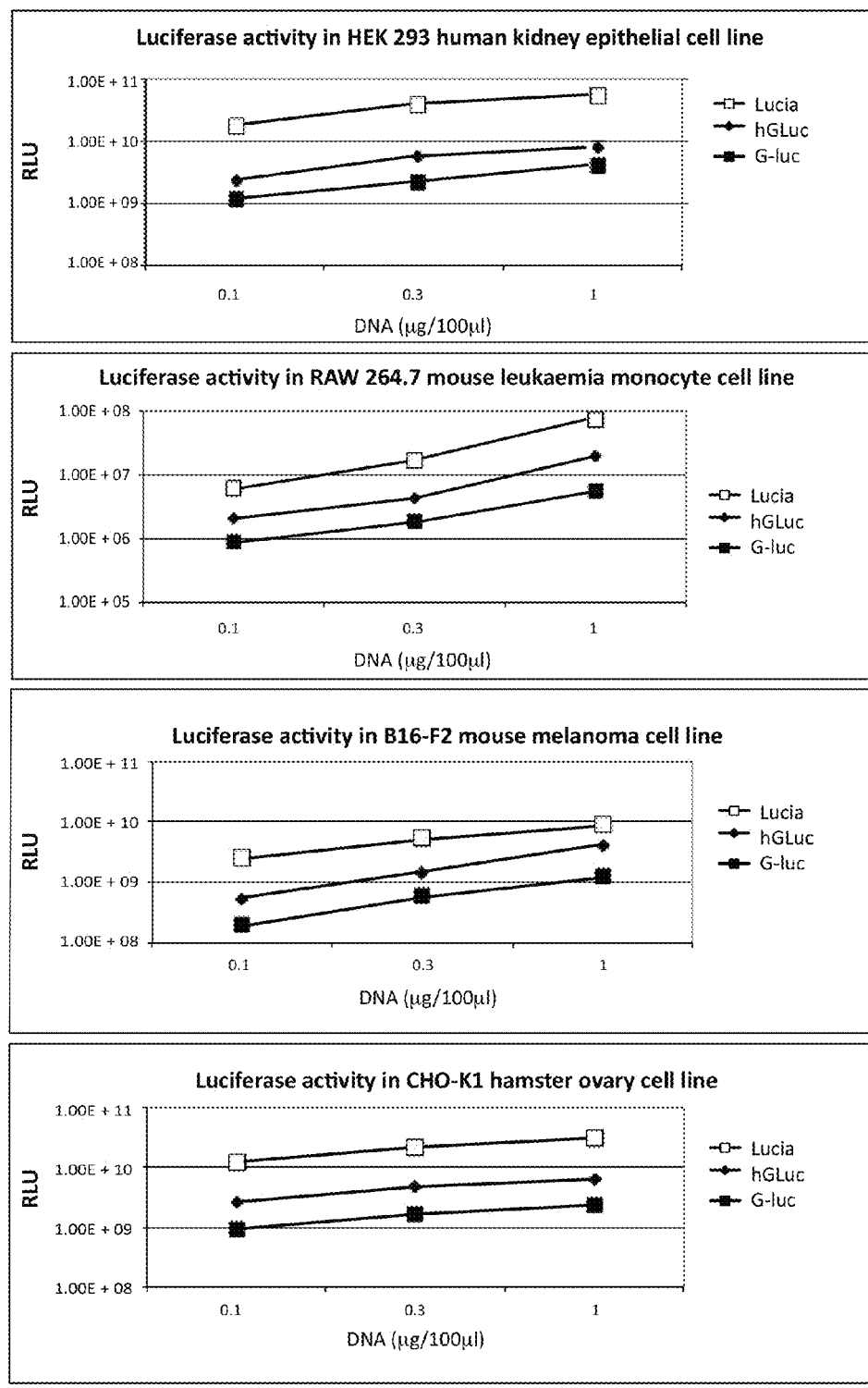

FIG. 8 shows the comparison of Lucia luciferase activity to that of hGLuc or the CpG-free G-luc expressed in different cell lines; HEK293 (ATCC #CRL-11268), RAW 264.7 (ATCC #TIB-71), B16-F2 (in house, origin from ATCC #CRL-6323) and CHO-K1 (ATCC #CCL-61).

FIG. 9 shows the nucleic acid sequence of the CpG-free Lucia expression cassette. Interferon-stimulated response elements (ISRE): 9-74 bp-Human ISG-54K minimal promoter: 85-328 bp-CDS: 329-958 bp/gene="SLuc"/product="Lucia pre-protein"-SV40 polyadenylation region: 969-1193 bp.

Nucleic acid sequence of the expression cassette is set forth as SEQ ID NO: 12.

FIG. 10 shows Lucia as a reporter gene in HEK293 and RAW 264.7 cell lines. Luciferase expression was determined in the supernatant of HEK293 cells and RAW 264.7 stably expressing Lucia under control of the I-ISG54 promoter (2934-15G54-Lucia and RAW-I-ISG54-Lucia, respectively) following 16 h incubation with human or murin IFN-α, transfected poly(dA:dT) and human TNF-α at the indicated doses in QUANTI-Luc™ (InvivoGen) using a Fluostar Optima (BMG Labtech).

Figure 11:
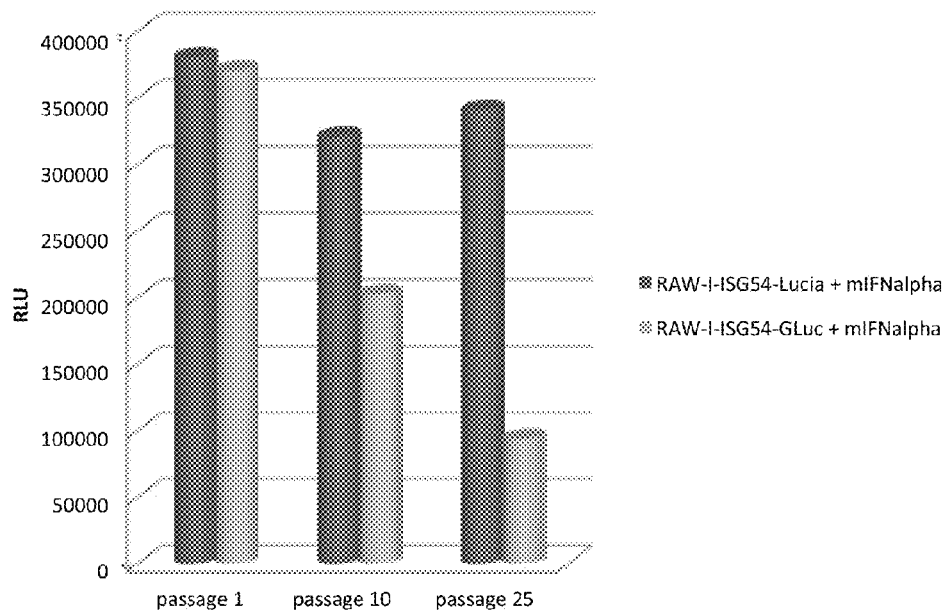

FIG. 11 shows the expression stability of Lucia versus hGLuc expression in RAW 267.4 cells after multiple subcultures. Subcultures of RAW 264.7 cells stably expressing Lucia or hGLuc under control of the I-ISG54 promoter (RAW-I-ISG54-Lucia and RAW-I-ISG54-hGLuc, respectively) were stimulated with 10 ng/ml of mouse IFN-α and were analyzed for luciferase expression in culture supernatant in QUANTI-Luc™ (InvivoGen) using a Fluostar Optima (BMG Labtech).

Figure 12:
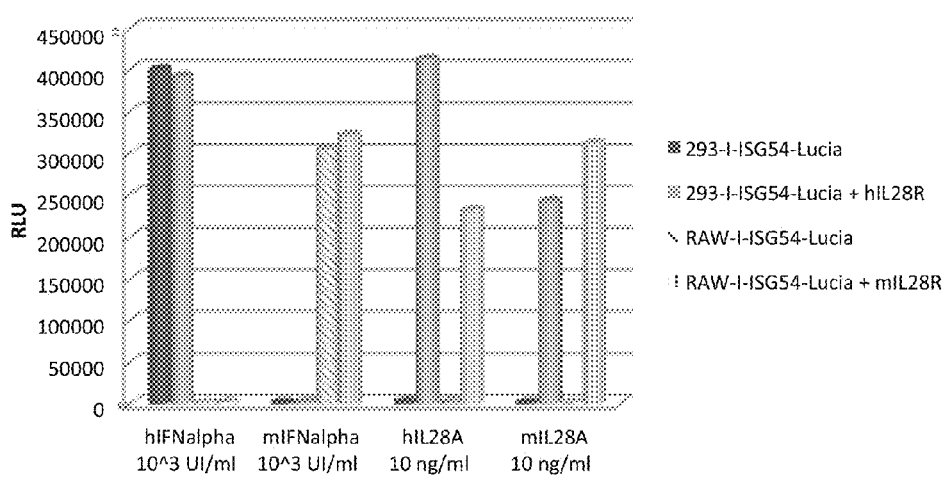

FIG. 12 shows the use of Lucia as reporter gene for the detection of IFN-lambda induction in HEK293 and RAW 264.7 cells. Luciferase expression was assessed in HEK293 cells or RAW 264.7 cells stably expressing Lucia under control of the I—ISG54 promoter (293-I-ISG54-Lucia and RAW-I-ISG54-Lucia, respectively) and co-expressing or not the type III IFN lambda receptor (IL28R) following 16 h incubation with human/mouse type I IFN (IFN-α) or human/mouse type III IFN (IL28A) at the indicated doses in QUANTI-Luc™ (InvivoGen) using a Fluostar Optima (BMG Labtech).

Figure 13:
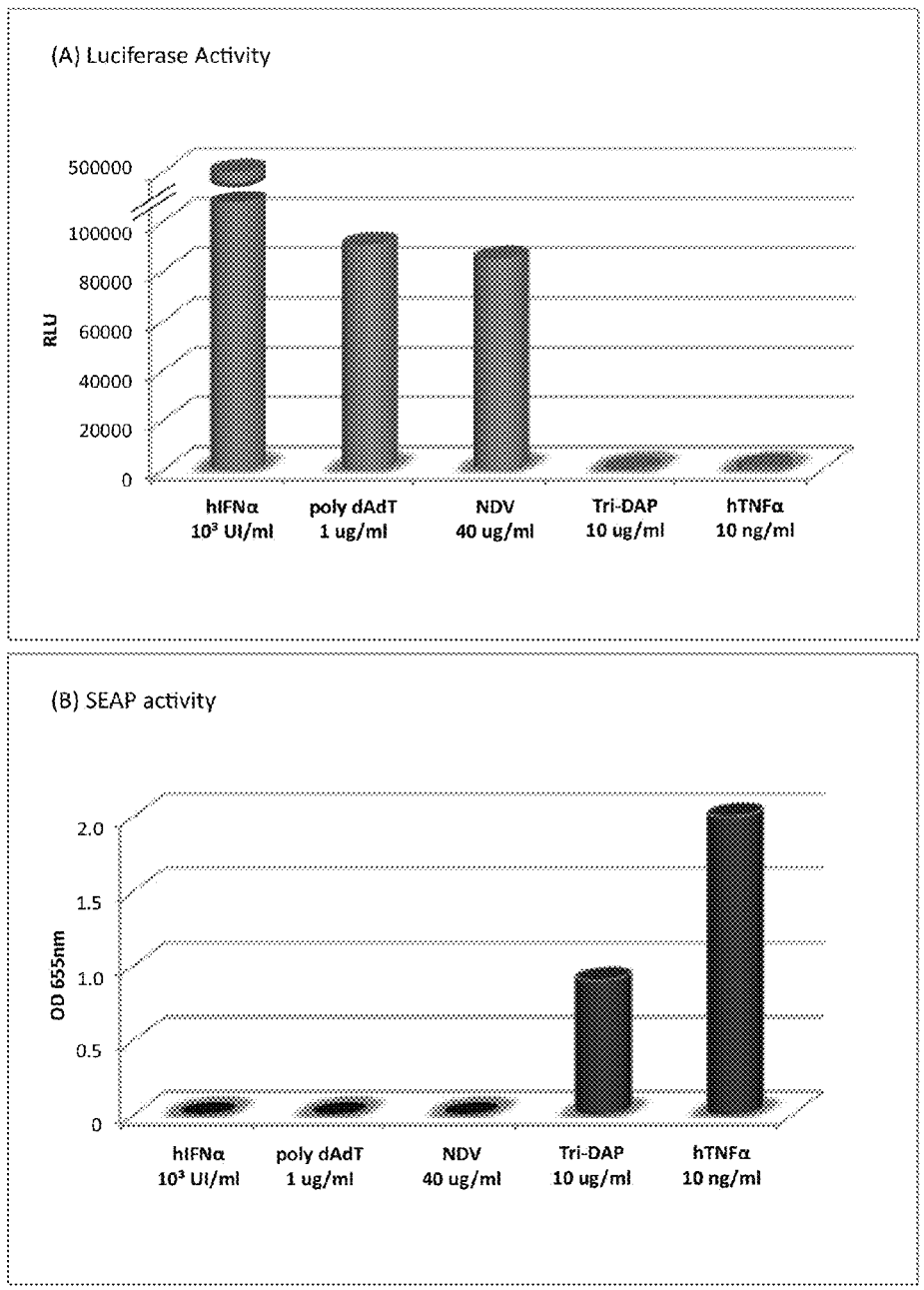

FIG. 13 shows the use of Lucia in dual reporter cell line: 293-I-ISG54-Lucia/AN-SEAP. Luciferase and SEAP activities were determined in HEK293 cells stably expressing Lucia under control of the I-ISG54 promoter and SEAPΔCpG under control of the AP-1/NF-κB promoter (293-I-ISG54-Lucia/AN-SEAP) following incubation with IFN inducers hIFN-α or transfected poly(dA:dT) or NDV (Newcastle Disease Virus). Cells were also treated with NF-κB-inducers TNF-α or Tri-DAP (NOD1 ligand). Luciferase activity was assessed in QUANTI-Luc™ (InvivoGen) after 48 h incubation using a Fluostar Optima (BMG Labtech). SEAP activity was assessed in QUANT1-Blue™ (InvivoGen) after 24 h using iMark™ Microplate Reader (BIO-RAD) in 96 well plates.

EXAMPLES

The inventors made several CpG-free variants of four copepod luciferases. The challenge is to obtain a CpG deleted gene that is codon optimized and retains mRNA structure to ensure high and sustained gene expression as well as retains or enhances activity of the protein expressed. The inventors demonstrated that the CpG-free variants derived of the luciferase genes, produced luciferases with lower activity compared to the wildtype proteins. Since their goal was to obtain a CpG-depleted luciferase with enhanced activity, the inventors rationalized the design of a completely new luciferase gene free of CpG motifs to generate a substantially more active luciferase protein than the most active known luciferase from *Gaussia*. The inventors have designed and synthesized a completely new secreted luciferase gene. This entirely synthetic CpG-free secreted luciferase gene is based on sequence alignment of various copepod luciferases among which is the *Gaussia* luciferase. The invention of this novel CpG-free luciferase gene is derived from nucleotide mutations resulting in multiple amino-acid changes compared to the corresponding luciferases. The new gene, named SLuc, displays higher and prolonged gene expression, and generates a secreted luciferase, named Lucia, which displays stronger luciferase activity compared to that generated by a codon-optimized hGLuc gene.

The strategy of the inventors was to synthesize several new randomized CpG-free sequences based on the known secreted luciferase genes. To this goal, the inventors performed an overlay extension PCR method of randomized oligonucleotide pair sequences corresponding to sequences of copepod luciferase genes, but where the first base of each non-conserved codon degenerated to each of the four DNA bases and avoiding any cytosine and guanines (CpGs) within the second and third bases, respectively. The randomized, putatively CpG-free genes obtained, were cloned into a mammalian expression vector and transformed into *E. coli* to undergo blue/white colony screening for an inserted recombinant DNA fragment. Since the luciferase activity cannot be detected in *E. coli*, recombinant plasmid DNA was purified from each white clone and verified for the correct sized insert, and then used individually to transfect a human cell line, HEK293, in multi-well plates. Luciferase activity was assayed from supernatants of each well to detect the few exhibiting an enhanced luciferase activity compared to wells transfected with a plasmid encoding a CpG-free GLuc gene, referred to herein as G-luc. Numerous rounds of screening allowed the isolation of positive plasmids, most of which contain some CpG dinucleotides within the randomized inserted sequence. Next was to obtain a completely CpG-free luciferase with high and sustained transgene expression giving strong luciferase activity proved challenging due to the multiple parameters at the level of gene expression and protein activity (Mutskov and Felsenfeld 2004; Bauer et al. 2010; Chodavarapu et al. 2011; Fath et al. 2011). Nevertheless, the inventors succeeded in isolating a completely new secreted luciferase gene, entirely devoid of CpGs and containing multiple amino acid changes that clearly distinguish this gene from the known secreted copepod luciferase genes. This gene, named SLuc, due to its high transgene expression, codes for a novel secreted luciferase protein, named Lucia, which displays enhanced luciferase activity compared to the codon-optimized hGLuc.

Generation and Testing of CpG-Free Versions of Secreted Copepod Luciferases

The inventors first attempted to identify a CpG-free secreted luciferase with strong luciferase activity. CpG-free nucleic acid sequences of the four known secreted copepod luciferase genes (GLuc from *Gaussia princeps*, MLuc from *Metrida longa*, MpLuc1 & MpLuc2 from *Metrida pacifica*) were obtained. The coding regions were optimized using an in-house software (Gencook) removing CpG dinucleotides and taking into account the codon usage, GC-content, mRNA structure and species-specific sequence motifs to optimize gene expression (Sequences shown in FIG. 1). These CpG-free genes were assembled by overlap extension PCR of hybridized oligonucleotides and inserted into the pSELECT-zeo-LacZ vector (InvivoGen). To serve as a control, the same method was employed to assemble the reference gene, the humanized coding sequence of *Gaussia* luciferase (hGLuc), commercially available from Prolume or New England Biolabs, which was re-synthetised and mutated at internal NcoI site (CCATGG=>CtATGG), to allow for insertion into the vector at NcoI and NheI sites. An overlap extension PCR method was performed to synthesize the CpG-free genes. This involved hybridization of complimentary oligonucleotides of 60 bases in length with 30 base-overlapping regions, entirely scanning the gene. Oligonucleotides flanking the gene were designed to contain the NcoI or NheI restriction sites for insertion into the corresponding sites in the pSELECT-zeo-LacZ vector. Thus the amplification of the various assembled oligonucleotides was carried out by PCR with a sense oligonucleotide containing a NcoI restriction site at the start codon and a reverse oligonucleotide containing a NheI restriction site after the stop codon. The detailed methodology is described below in the synthesis and construction of the CpG-free randomized genes. The final PCR fragments were digested with the NcoI and NheI restriction enzymes and cloned into the pSELECT-zeo-LacZ plasmid linearized with NcoI and NheI.

The CpG-free versions of the four copepod luciferase genes were assayed for the production of a secreted luciferase protein with strong luciferase activity, comparable to the reference gene hGLuc. Luciferase activity in the supernatant of HEK293 cells (from ATCC, CRL-11268™) following transfection with the various recombinant plasmids (pSELECT-zeo-GLuc-CpGfree, pSELECT-zeo-MLuc-CpGfree, pSELECT-zeo-MpLuc1-CpGfree, pSELECT-zeo-MpLuc2-CpGfree, and pSELECT-zeo-hGLuc) was determined. The luciferase activity obtained by expression of the hGLuc gene was always superior to that of the four CpG-free luciferases in three separate experiments (data not shown). Therefore, an improved version of these CpG-free genes was necessary to increase the level of luciferase activity of the corresponding expressed protein.

Synthesis and Construction of Randomized CpG-Free Luciferase Genes

In order to generate a new and improved CpG-free secreted luciferase gene, the inventors first performed alignments of the four CpG-free luciferase sequences (Alignment presented in FIG. 1). A working sequence was determined, identifying both conserved and non-conserved codons. Each non-conserved codon was randomized by replacing the first base of the codon with N representing any one of the 4 bases, and avoiding any cytosine and guanines (CpGs) within the second and third bases, respectively. Since the GLuc sequence is around 120 base pairs shorter compared to the Metrida luciferases, new peptidic sequences were introduced of variable length with their complementary counterpart. Oligonucleotides were synthesized for every degenerate sequence and the CpG-free randomized genes were assembled by an overlap extension PCR method. The method was carried out in three steps; the first step consisted of phosphorylation of the oligonucleotides of the coding strand, the second step combined all the oligonucleotides of both strands by hybridization and ligation and, in the final step, the gene was amplified by PCR. The Lucia gene, SLuc, was assembled using the oligonucleotides shown in FIG. 2.

In the first step, oligonucleotides corresponding to the coding strand, were phosphorylated according to the following procedure: 1 µl of each one of the oligonucleotides taken up in water at 250 µM were mixed in a micro-centrifuge tube containing water so as to bring the final solution to a concentration of 100 µmol per 65 µl. 5 µl of this solution was then mixed with 10 µl of 0.10-times concentrated polynucleotide kinase buffer, 0.4 µl of a 50 mM ATP solution, 85 µl of water and 1 µl of the enzyme (at 10 Units/A, and the entire mixture was incubated for 4 hours at 37° C. (solutions A & A'). For the second step, a solution of the oligonucleotides of the non-coding strand was made up by mixing 1 µl of each oligonucleotide and 1 µl of primers flanking the gene to introduce NcoI and NheI restriction sites for cloning into the plasmid vector. 41 µl (or 40 µl) of water was added to the oligonucleotides in order to obtain a final solution at 54 µmol per µl (solutions B & B'). Assembly of the synthesized genes was carried out first by mixing 10 µl of solution A (or A'), 1 µl of solution B (or B'), 6 µl of a 100 mM KCl solution, 3 µl of a 0.5% NP-40 solution, 4 µl of a 50 mM MgCl$_2$ solution, 3 µl of a 10 mM ATP solution and 7.5 µl of Pfu ligase (30 Units). The mixture was then heated in a programmable thermocycler for 3 minutes at 95° C., then 3 minutes at 80° C., before undergoing 3 cycles of one minute at 95° C., followed by a change from 95° C. to 70° C. in 1 minute, followed by a change from 70° C. to 55° C. in 1 hour and, finally, 2 hours at 55° C. Then in the final step, the mixtures of the assembled oligonucleotides were amplified using the flanking primers; the forward primer sequence containing a NcoI restriction site and the reverse primer containing a NheI restriction site. The mixed amplification products (from 600 to 660 bp) were separated by gel electrophoresis and purified. The synthesized gene fragments were then digested with the NcoI and NheI restriction enzymes and subsequently cloned into the plasmid pSELECT-zeo-LacZ (InvivoGen) linearized with NcoI and NheI. Each potential recombinant plasmid generated was transformed into the bacterial strain *E. coli* GT116 (InvivoGen), and white colony selection on FastMedia™ Zeo XGal Agar medium (InvivoGen) was performed to select for plasmids with integration of a synthesized gene disrupting the Lac Z gene in the vector. Individual white colonies were amplified and the recombinant plasmids were purified using a DNA plasmid purification kit (Macherey-Nagel). Recombinant plasmids were verified for the correct size gene insert by restriction digest using NcoI and NheI restriction enzymes.

Assaying for Luciferase Activity

Since assaying secreted luciferases must be performed in mammalian cells, the recombinant plasmids (pSELECT-zeo-'synthesized gene' or pSELECT-zeo-hGLuc) otherwise completely identical apart from the luciferase gene inserted, were expressed in a human mammalian cell line and screened for luciferase protein activity as described below. HEK293 cells were cultured in 96 well plates and in each well, cells were transfected with one individual recombinant plasmid DNA containing a randomized gene, using LyoVec™ (InvivoGen). Subsequent to transfection and production of protein, secreted luciferase activity was measured by bioluminescence quantification of the cell culture media using in a microplate luminometer (FLUOstar OPTIMA from BMG Labtech). Multiple rounds of screening (using ten 96 well plates) led to the identification of a large panel of randomized gene variants that produced secreted luciferases with diverse activities, ranging from zero to high when compared to the luciferase produced from the reference hGLuc gene (expressed by transfection of pSELECT-zeo-hGLuc). The randomized gene variants producing secreted luciferases that showed high luciferase activity or comparable to the codon optimized *Gaussia* luciferase were selected for DNA sequence analysis of the corresponding transfected plasmid DNA. Of the improved variants identified, most variants contained mutations generating new amino-acids and many variants contained CpG dinucleotides, due to the randomization of the first base of each non-conserved codon. A further round of screening involved selecting for the variants that were completely devoid of CpG dinucleotides, and the sequence of the best-improved CpG-free gene was obtained. This synthetic CpG free gene with enhanced expression codes for a novel secreted protein with a strong luciferase activity that has been named Lucia. The gene sequence of Lucia gene is shown in FIG. 3 and SEQ. ID NO. 1. The amino acid sequence of pre-protein Lucia is shown in FIG. 4 and SEQ. ID NO. 2. The alignment of the Lucia pre-protein with the four known secreted copepod luciferases is given in FIG. 5. Several monoclonal antibodies against Lucia were isolated after hydrodynamic injection of the pSELECT plasmid expressing Lucia and fusion of splenocytes of immunized mice with the myeloma P3X63-Ag8.653 cell line (ATCC #CLR-1580), according to a well established procedure. The Lucia neutralizing monoclonal antibody J3-3B6 (InvivoGen) was fixed on NHS-Activated sepharose (GE Healthcare) and used for chromatography affinity purification of Lucia from the supernatant of HEK293 cultures transfected with the Lucia expressing pSELECT plasmid. The Edman degradation of the N-terminal of the purified protein having luciferase activity revealed that the first five consecutive amino acids are KPTEI. Therefore the deduced amino acid sequence of the mature secreted Lucia protein is shown in FIG. 6 and SEQ.ID NO: 3. The diversity in nucleotide sequence of the Lucia gene compared with the CpG-free G-luc sequence and the hGLuc gene sequence is shown in the nucleotide alignment in FIG. 7. The superior activity of the Lucia luciferase protein when expressed in several cell lines compared to the hGLuc and the CpG-free G-luc luciferases is demonstrated in FIG. 8.

EXAMPLES FOR CARRYING OUT THE INVENTION

Hereinafter the present invention will be explained with specific reference to examples. Although the inventors describe one mode of use in the examples, the scope is not limited to these specific examples. Taking into consideration the complexities in generating a CpG-free luciferase with sustained transgene expression and strong luciferase activity, (Mutskov and Felsenfeld 2004; Bauer et al. 2010; Chodavarapu et al. 2011; Fath et al. 2011), the inventors have synthesized a completely new luciferase gene to be exploited as a reporter gene in live cell-based assays.

In Example 1A, the inventors describe the construction of a CpG-free expression cassette of the Lucia gene placed under the control of an IFN-inducible promoter to provide sensitive species-specific cell-based reporter assays for type I interferons; a HEK293 stable cell line for the detection of human type I interferons and a RAW 264.7 stable cell line for the detection of mouse type I interferons. In Example 1B the inventors demonstrate the long lasting transgene expression of the SLuc cassette in cells compared to that of hGLuc, after multiple subcultures of different clones. The inventors demonstrate in Example 2, a cell line stably expressing Lucia and co-transfected with IL28R, the IFN-lambda receptor, to successfully generate a non-species-specific IFN-lambda (or IL-28) reporter cell line. Furthermore, in Example 3, the inventors demonstrate the application to generate a stable dual reporter cell line, combining bioluminescence assay of luciferase activity and a colorimetric assay of alkaline phosphatase activity. Stable cell lines expressing the Lucia reporter gene were co-transfected with a CpG-free transcriptional unit coding for a secreted embryonic alkaline phosphatase (SEAP) reporter gene, allowing for concomitant monitoring of two distinct signalling pathways. In the example, the dual reporter cell line can monitor the IFN pathway and the AP-1/NK-κB pathway, which can be used to distinguish an anti-viral response and an inflammatory response from samples. These examples demonstrate the application of the Lucia gene as a stable reporter luciferase to sensitively monitor signalling pathways in cells, important in inflammation and cancer.

Example 1A

Construction of a CpG-Free Expression Cassette of the Lucia Gene to Generate a Sensitive Cell-Based Reporter Assay for Interferon Induction in HEK293 or RAW 264.7 Cell Lines The Lucia gene, SLuc, was used as a reporter gene in HEK293 cells (human embryonic kidney cell line; ATCC #CRL-11286) and RAW 264.7 cells (mouse leukaemia monocyte macrophage cell line; ATCC #TIB-71) to generate type I and type III interferons reporter cell lines. SLuc was placed under the control of an interferon-inducible promoter (I-ISG54) comprising five interferon-stimulated response elements (ISRE) and the minimal promoter of the human ISG-54K (Interferon Stimulation of a Gene encoding a 54 kDa protein) gene. The inventors chose this promoter because among the known IFN-induced proteins, endogenous ISG-54K expression was the best induced by interferon regulatory factor 3 (IRF3), which has a key involvement in anti-viral responses (Grandvaux et al. 2002). The minimal promoter of the human ISG-54K gene contains two ISRE sites and was described as fully inducible by type I interferons (IFN-α and IFN-β) and interferon regulatory factors (IRFs) (Wathelet et al. 1988; Grandvaux et al. 2002). Upstream of the promoter, a synthetic sequence containing five direct-repeated copies of CpG-free ISRE consensus sequences (AGTTTCNNTTTCC/T) deduced from type I IFN-regulated promoters was added. The pNiFty-I-ISG54-SLuc plasmid containing the interferon-inducible expression cassette was constructed from the pNiFty3-I-SEAP plasmid (InvivoGen) by first replacing an SdaI-NcoI fragment containing the IFN-β minimal promoter with an SdaI-NcoI fragment consisting of the ISG54 minimal promoter and then replacing the NcoI-NheI fragment containing the human secreted embryonic alkaline phosphatase (SEAP) gene with a NcoI-NheI fragment containing the Lucia gene. The three remaining CpGs of the minimal promoter sequence were replaced by TpGs using PCR method. The polyadenylation sequence of the cassette comes from the late SV40 polyadenylation region, which is naturally CpG-free. The entire sequence of the Lucia expression cassette completely devoid of CpGs cloned in the pNiFty-I-ISG54-SLuc plasmid is shown in FIG. 9.

Inducible Lucia luciferase expression was assessed in HEK293 and RAW 264.7 cells stably transfected with pNiFty-I-ISG54-SLuc. To this end, 250 000 cells per well in DMEM were seeded in 12-well microtiter plates and incubated at 37° C. overnight. Transfections were performed using the transfection reagent LyoVec™ (InvivoGen) according to the manufacturer's instructions. Transfected cells were incubated 3 days at 37° C. Stable cell lines were generated by selecting the transfected cells with 100 ng/ml Zeocin and determining the luciferase activity in supernatants in induced ($10^3$ UI/ml IFN-α and unstimulated conditions. FIG. 10 depicts the results of the bioluminescence measurement of HEK293 and RAW 264.7 cells stably transfected with pNiFty-I-ISG54-SLuc following 16 h incubation with different molecules. IFN-αinductions are species-specific and, as expected, IFN-α but not TNFα induces luciferase expression.

Example 1B

Stability of Lucia Versus hGLuc Expression in RAW 264.7 After Multiple Subcultures The pNiFty-I-ISG54-hGLuc plasmid was constructed from the pNiFty-I-ISG54-SLuc plasmid by substituting the NcoI-NheI Lucia gene fragment with the NcoI-NheI hGLuc fragment. The luciferase expression cassette in pNiFty-I-ISG54-hGLuc contains 32 CpG motifs.

Inducible luciferase expression was determined in RAW 264.7 cells stably transfected with the pNiFty-I-ISG54-hGLuc plasmid. To this end, 250,000 cells per well in DMEM were seeded on 12-well microtiter plates and incubated at 37° C. overnight. Transfections were performed using the transfection reagent LyoVec™ (InvivoGen) according to the manufacturer's instructions. Transfected cells were incubated 3 days at 37° C. Stable cell lines were prepared by selecting the transfected cells with 100 μg/ml Zeocin and determining the luciferase activity in supernatants in induced ($10^3$ UI/ml IFN-α) and unstimulated conditions.

Subcultures of stable RAW 264.7 cell lines transfected with pNiFty-I-ISG54-SLuc or pNiFty-I-ISG54-hGLuc (RAW-I-ISG54-Lucia and RAW-I-ISG54-hGLuc, respectively) were prepared as follows: 25,000 cells per well in DMEM were plated on 12 well microtiter plates and incubated 3 days at 37° C. At this time (passage 1), cells were trypsinized and counted with a Z1 Beckman Coulter counter. 25,000 cells per well in DMEM were plated on 12 well microtiter plates to prepare passage 2, and 10,000 cells per well in DMEM with $10^3$ UI/ml IFN-α were plated on a 96-well microtiter plate. The 96-well microtiter plate was incubated 16 h at 37° C. then luciferase activity determined Subcultures were prepared up to passage 25. Luciferase expression by the 32 CpG containing cassette in RAW-I-ISG54-hGLuc declines as the number of cell passages increase, in contrast to the luciferase expressed by the CpG-free cassette in RAW-I-ISG54-Lucia cells. FIG. 11 depicts the full inducibility and thus expression stability of Lucia compared to hGLuc.

Example 2

Detection of IFN-Lambda Induction in RAW 264.7 and HEK293 Cells Stably Expressing IL28R The Lucia reporter gene was used to generate type I and type III IFN reporter cells derived from the human HEK293 cells and mouse RAW 264.7 macrophages. Type III IFNs include IFN-lambda also called IL-28. Type I and type III IFN systems both signal through the JAK1/TYK2 tyrosine kinases and the transcription factor complex ISGF3 consisting of STAT1, STAT2 and IRF9. The receptor complex for type III IFN is composed of IFN-lambdaR1 (also termed IL28Ralpha or CRF2-12), which is specific for the type III IFNs, and the accessory receptor chain IL10R2 (also designed IL10Rbeta or CRF2-4). Unlike type I IFN receptor complexes that are expressed in most cell types, IFN-lambdaR1 demonstrates a restricted pattern of expression limiting the response to type III IFNs to epithelial cells in vivo (Donnelly and Kotenko, 2010). Therefore 293-I-ISG54-Lucia and RAW-I-ISG54-Lucia cells stably expressing the IL28 receptor alpha (IL28Rα) were generated by transfection with the InvivoGen expression plasmids pUNO-hIL28Rα (human gene) or pUNO-mIL28Rα (mouse gene), respectively. To this end, 250,000 cells per well in DMEM were plated on 12 well microtiter plates and incubated at 37° C. overnight. Transfections were performed using the transfection reagent LyoVec™ (InvivoGen) according to the manufacturer's instructions. Transfected cells were incubated 3 days at 37° C. Stable cell lines were prepared by selecting the transfected cells with 30 ng/ml Blasticidin and determining the luciferase activity in supernatants in induced (10 ng/ml IL28) and unstimulated conditions.

FIG. 12 depicts the results of the bioluminescence measurement of 293-I-ISG54-Lucia and RAW-I-ISG54-Lucia cells stably transfected with a pUNO-IL28R plasmid following 16 h incubation with human or mouse type I interferon (IFN-α) and human or mouse type III interferon (IL28). In contrast to type I IFN, type III interferon is not species-specific.

Example 3

Dual Reporter Cell Line:
293-I-ISG54-Lucia/AN-hSEAP

The Lucia reporter gene was associated with a secreted embryonic alkaline phosphatase (SEAP) reporter gene to generate HEK293 reporter cells that allow the concomitant monitoring of the IFN pathway (anti-viral response) and the AP-1/NF-κB (AN) pathway (inflammatory response). The pNiFty3-AN-SEAPΔCpG plasmid was constructed from the pNiFty3-AN-SEAP plasmid (InvivoGen) by replacing an hSEAP-containing NcoI-NheI fragment with an NcoI-NheI fragment containing a CpG-free hSEAP (SEAPΔCpG) gene from the pSELECT-zeo-hSEAP plasmid (InvivoGen). The SEAP expression cassette in the pNiFty3-AN-SEAPΔCpG plasmid contains no CpGs. The dual reporter 293-I-ISG54-Lucia/AN-SEAP cell line was generated by co-transfecting the 2934-I-ISG54-Lucia cell line with the pNiFty3-AN-SEAPΔCpG and pSELECT-puro (InvivoGen) plasmids at a 10/1 ratio respectively. To this end, 250,000 cells per well in DMEM were plated on 12 well microtiter plates and incubated at 37° C. overnight. Transfections were performed using the transfection reagent LyoVec™ (InvivoGen) according to the manufacturer's instructions. Transfected cells were incubated 3 days at 37° C. Stable cell lines were prepared by selecting transfected cells with 1 ng/ml puromycin and determining the luciferase and SEAP activities in supernatants in unstimulated condition or following 16 h incubation with 10 ng/ml of IFN-α or with 10 ng/ml of TNF-α. FIG. 13 depicts the results of the bioluminescence measurement (A) and SEAP activity (B) of the 293-I-ISG54-Lucia/AN-SEAP cell line following 16 h incubation with IFN inducers; human IFN-α, poly(dA:dT) at the indicated doses or for 48 h incubation with NDV (heat killed Newcastle disease virus) or following incubation with NF-κB inducers; human TNFα for 16 h or 48 h incubation with the NOD1 ligand, Tri-DAP. As expected, SEAP is detected only after TNFα or Tri-DAP stimulation (which mediate the activation of transcription factors AP1 and NF-κB) whereas Lucia activity is detected following IFN-α, poly(dA:dT) stimulations (which trigger the activation of IRF transcription factors) and partially after exposure to NDV.

REFERENCES

Throughout this application, various references describe the state of the art to which this invention pertains. The disclosures of these references are hereby incorporated by reference into the present disclosure.

PATENTS

Bryan et al. 2001. U.S. Pat. No. 6,232,107 B1. Luciferases, fluorescent proteins, nucleic acids encoding the luciferases and fluorescent proteins and the use thereof in diagnostics, high throughput screening and novelty items. (PCT Pub. WO 1999/049019).

Drocourt et al. 2007. U.S. Pat. No. 7,244,609 B2. Synthetic genes and bacterial plasmids devoid of CpG. (PCT Pub WO02/072846).

Golz et al. 2002. WO 02/42470. Isolated luciferases and the use thereof

Golz et al. 2010. U.S. Pat. No. 0,105,090 A1. Secreted luciferase MLuc7 and use thereof.

Kim et al. 2010. WO/2010/119721. Stable artificial bioluminescent enzyme having super-high brightness.

Takenaka 2009. U.S. Pat. No. 0,233,320 A1. Gene encoding novel luciferase. (PCT pub WO 2006/061906).

Tannous and Maguire 2011. WO/2011/002924. *Gaussia* luciferase variant for high throughput screening.

PUBLICATIONS

Barlow D P. 2010. Genomic Imprinting: A Mammalian Epigenetic Discovery Model. *Annu Rev Genet.*

Bauer A P, Leikam D, Krinner S, Notka F, Ludwig C, Längst G, Wagner R. 2010. The impact of intragenic CpG content on gene expression. *Nucleic Acids Res* 38: 3891-3908.

Bergbauer M, Kalla M, Schmeinck A, Göbel C, Rothbauer U, Eck S, Benet-Pagés A, Strom T M, Hammerschmidt W. 2011. CpG-methylation regulates a class of Epstein-Barr virus promoters. *PLoS Pathog* 6: e1001114.

Brooks A R, Harkins R N, Wang P, Qian H S, Liu P, Rubanyi G M. 2004. Transcriptional silencing is associated with extensive methylation of the CMV promoter following adenoviral gene delivery to muscle. *J Gene Med* 6: 395-404.

Chevalier-Mariette C, Henry I, Montfort L, Capgras S, Forlani S, Muschler J, Nicolas J F. 2003. CpG content affects gene silencing in mice: evidence from novel transgenes. *Genome Biol* 4: R53.

Chodavarapu R K, Feng S, Bernatavichute Y V, Chen P Y, Stroud H, Yu Y, Hetzel J A, Kuo F, Kim J, Cokus S J et al. 2011. Relationship between nucleosome positioning and DNA methylation. *Nature* 466: 388-392.

Chung E, Yamashita H, Au P, Tannous B A, Fukumura D, Jain R K. 2009. Secreted *Gaussia* luciferase as a biomarker for monitoring tumor progression and treatment response of systemic metastases. *PLoS One* 4: e8316.

Dalle B, Rubin J E, Alkan O, Sukonnik T, Pasceri P, Yao S, Pawliuk R, Leboulch P, Ellis J. 2005. eGFP reporter genes silence LCRbeta-globin transgene expression via CpG dinucleotides. *Mol Ther* 11: 591-599.

De A, Gambhir S S. 2005. Noninvasive imaging of protein-protein interactions from live cells and living subjects using bioluminescence resonance energy transfer. *FASEB J* 19: 2017-2019.

de Wet J R, Wood K V, Helinski D R, DeLuca M. 1985. Cloning of firefly luciferase cDNA and the expression of active luciferase in *Escherichia coli*. *Proc Natl Acad Sci U S A* 82: 7870-7873.

Donnelly R P and Kotenko S V. 2010. Interferon-Lambda: A new addition to an old family. *Journal of Interferon and Cytokine Research* 30: 555-64.

Enjalbert B, Rachini A, Vediyappan G, Pietrella D, Spaccapelo R, Vecchiarelli A, Brown A J, d'Enfert C. 2009. A multifunctional, synthetic *Gaussia princeps* luciferase reporter for live imaging of *Candida albicans* infections. *Infect Immun* 77: 4847-4858.

Esteller M. 2008. Epigenetics in cancer. *The New England journal of medicine* 358: 1148-1159.

Fan F, Wood K V. 2007. Bioluminescent assays for high-throughput screening. *Assay Drug Dev Technol* 5: 127-136.

Fath S, Bauer A P, Liss M, Spriestersbach A, Maertens B, Hahn P, Ludwig C, Schäfer F, Graf M, Wagner R. 2011. Multiparameter RNA and codon optimization: a standardized tool to assess and enhance autologous mammalian gene expression. *PLoS One* 6: e17596.

Frommer M, McDonald L E, Millar D S, Collis C M, Watt F, Grigg G W, Molloy P L, Paul C L. 1992. A genomic sequencing protocol that yields a positive display of 5-methylcytosine residues in individual DNA strands. *Proc Natl Acad Sci USA* 89: 1827-1831.

Girault I, Tozlu S, Lidereau R, Bieche I. 2003. Expression analysis of DNA methyltransferases 1, 3A, and 3B in sporadic breast carcinomas. *Clinical cancer research: an official journal of the American Association for Cancer Research* 9: 4415-4422.

Graessmann A, Sandberg G, Guhl E, Graessmann M. 1994. Methylation of single sites within the herpes simplex virus tk coding region and the simian virus 40 T-antigen intron causes gene inactivation. *Mol Cell Biol* 14: 2004-2010.

Grandvaux N, Servant M J, tenOever B, Sen G C, Balachandran S, Barber G N, Lin R, Hiscott J. 2002. Transcriptional profiling of interferon regulatory factor 3 target genes: direct involvement in the regulation of interferon-stimulated genes. *J. Virol.* 76:5532-9.

Griesenbach U, Vicente C C, Roberts M J, Meng C, Soussi S, Xenariou S, Tennant P, Baker A, Baker E, Gordon C et al. 2011. Secreted *Gaussia* luciferase as a sensitive reporter gene for in vivo and ex vivo studies of airway gene transfer. *Biomaterials* 32: 2614-2624.

Haugwitz M, Nourzaie 0, Garachtchenko T, Hu L, Gandlur S, Olsen C, Farmer A, Chaga G, Sagawa H.2008. Multiplexing bioluminescent and fluorescent reporters to monitor live cells. *Current chemical genomics* 1: 11-19.

Hodges B L, Taylor K M, Joseph M F, Bourgeois S A, Scheule R K. 2004. Long-term transgene expression from plasmid DNA gene therapy vectors is negatively affected by CpG dinucleotides. *Mol Ther* 10: 269-278.

Hyde S C, Pringle I A, Abdullah S, Lawton A E, Davies L A, Varathalingam A, Nunez-Alonso G, Green A M, Bazzani R P, Sumner-Jones S G et al. 2008. CpG-free plasmids confer reduced inflammation and sustained pulmonary gene expression. *Nature biotechnology* 26: 549-551.

Inouye S, Ohmiya Y, Toya Y, Tsuji F I. 1992. Imaging of luciferase secretion from transformed Chinese hamster ovary cells. *Proc Natl Acad Sci USA* 89: 9584-9587.

Kim S B, Suzuki H, Sato M, Tao H. 2011. Superluminescent Variants of Marine Luciferases for Bioassays. *Anal Chem*.

Krieg A M, Yi A K, Matson S, Waldschmidt T J, Bishop G A, Teasdale R, Koretzky G A, Klinman D M. 1995. CpG motifs in bacterial DNA trigger direct B-cell activation. *Nature* 374: 546-549.

Lorenz W W, McCann R O, Longiaru M, Cormier M J. 1991. Isolation and expression of a cDNA encoding *Renilla reniformis* luciferase. *Proc Natl Acad Sci USA* 88: 4438-4442.

Lwa T R, Tan C H, Lew Q J, Chu K L, Tan J, Lee Y Y, Chao S H. 2010. Identification of cellular genes critical to recombinant protein production using a *Gaussia* luciferase-based siRNA screening system. *J Biotechnol* 146: 160-168.

Maguire C A, Deliolanis N C, Pike L, Niers J M, Tjon-Kon-Fat L A, Sena-Esteves M, Tannous B A. 2009. *Gaussia* luciferase variant for high-throughput functional screening applications. *Anal Chem* 81: 7102-7106.

Markova S V, Golz S, Frank L A, Kalthof B, Vysotski E S. 2004. Cloning and expression of cDNA for a luciferase from the marine copepod *Metridia longa*. A novel secreted bioluminescent reporter enzyme. *J Biol Chem* 279: 3212-3217.

Marks P, Rifkind R A, Richon V M, Breslow R, Miller T, Kelly W K. 2001. Histone deacetylases and cancer: causes and therapies. *Nature reviews Cancer* 1: 194-202.

Medzhitov R. 2001. Toll-like receptors and innate immunity. *Nature reviews Immunology* 1: 135-145.

Mitsui M, Nishikawa M, Zang L, Ando M, Hattori K, Takahashi Y, Watanabe Y, Takakura Y. 2009. Effect of the content of unmethylated CpG dinucleotides in plasmid DNA on the sustainability of transgene expression. *J Gene Med* 11: 435-443.

Mutskov V, Felsenfeld G. 2004. Silencing of transgene transcription precedes methylation of promoter DNA and histone H3 lysine 9. *The EMBO journal* 23: 138-149.

Nakajima Y, Kobayashi K, Yamagishi K, Enomoto T, Ohmiya Y. 2004. cDNA cloning and characterization of a secreted luciferase from the luminous Japanese ostracod, *Cypridina noctiluca*. *Biosci Biotechnol Biochem* 68: 565-570.

Pfeifer G P, Tanguay R L, Steigerwald S D, Riggs A D. 1990. In vivo footprint and methylation analysis by PCR-aided genomic sequencing: comparison of active and inactive X chromosomal DNA at the CpG island and promoter of human PGK-1. *Genes Dev* 4: 1277-1287.

Prescher J A, Contag C H. 2010. Guided by the light: visualizing biomolecular processes in living animals with bioluminescence. *Curr Opin Chem Biol* 14: 80-89.

Prosch S, Stein J, Staak K, Liebenthal C, Volk H D, Krüger D H. 1996. Inactivation of the very strong HCMV immediate early promoter by DNA CpG methylation in vitro. *Biol Chem Hoppe Seyler* 377: 195-201.

Ray P, Gambhir S S. 2007. Noninvasive imaging of molecular events with bioluminescent reporter genes in living subjects. *Methods Mol Biol* 411: 131-144.

Sadikot R T, Blackwell T S. 2008. Bioluminescence: imaging modality for in vitro and in vivo gene expression. *Methods Mol Biol* 477: 383-394.

Takenaka Y, Masuda H, Yamaguchi A, Nishikawa S, Shigeri Y, Yoshida Y, Mizuno H. 2008. Two forms of secreted and thermostable luciferases from the marine copepod crustacean, *Metridia pacifica*. *Gene* 425: 28-35.

Tannous B A, Kim D E, Fernandez J L, Weissleder R, Breakefield X O. 2005. Codon-optimized *Gaussia* luciferase cDNA for mammalian gene expression in culture and in vivo. *Mol Ther* 11: 435-443.

Tannous B A, Teng J. 2011. Secreted blood reporters: Insights and applications. *Biotechnol Adv* 29: 997-1003.

Thompson E M, Adenot P, Tsuji F I, Renard J P. 1995. Real time imaging of transcriptional activity in live mouse preimplantation embryos using a secreted luciferase. *Proc Natl Acad Sci USA* 92: 1317-1321.

Thompson E M, Nagata S, Tsuji F I. 1989. Cloning and expression of cDNA for the luciferase from the marine ostracod *Vargula hilgendorfii*. *Proc Natl Acad Sci USA* 86: 6567-6571.

Thompson E M, Nagata S, Tsuji F I. 1990. *Vargula hilgendorfii* luciferase: a secreted reporter enzyme for monitoring gene expression in mammalian cells. *Gene* 96: 257-262.

Tilghman S M. 1999. The sins of the fathers and mothers: genomic imprinting in mammalian development. *Cell* 96: 185-193.

Verhaegent M, Christopoulos T K. 2002. Recombinant *Gaussia* luciferase. Overexpression, purification, and analytical application of a bioluminescent reporter for DNA hybridization. *Anal Chem* 74: 4378-4385.

Wathelet M G, Clauss 1M, Content J, Huez G A. 1988. Regulation of two interferon-inducible human genes by interferon, poly(rI).poly(rC) and viruses. *Eur J. Biochem.* 174: 323-9.

Welsh J P, Patel K G, Manthiram K, Swartz J R. 2009. Multiply mutated Gaussia luciferases provide prolonged and intense bioluminescence. *Biochem Biophys Res Commun* 389: 563-568.

Yagi K. 2007. Applications of whole-cell bacterial sensors in biotechnology and environmental science. *Appl Microbiol Biotechnol* 73: 1251-1258.

Yew N S, Zhao H, Przybylska M, Wu I H, Tousignant J D, Scheule R K, Cheng S H. 2002. CpG-depleted plasmid DNA vectors with enhanced safety and long-term gene expression in vivo. *Mol Ther* 5: 731-738.

The invention claimed is:

1. An isolated nucleic acid molecule, the nucleic acid encoding a preprotein comprising:
    a signal peptide; and
    a protein having luciferase activity,
    wherein, said nucleic acid molecule is devoid of CpG, and said protein having luciferase activity comprises an amino acid sequence having at least 95% identity to the amino acid sequence set forth as SEQ ID NO: 3.

2. The isolated nucleic acid molecule according to claim 1, comprising the nucleic acid sequence set forth as SEQ ID NO: 1.

3. The isolated nucleic acid molecule according to claim 1, wherein said protein having luciferase activity comprises the amino acid sequence having at least 95% identity to the amino acid sequence set forth as SEQ ID NO: 3 when the said protein is secreted from cells.

4. An expression vector, comprising the nucleic acid molecule according to claim 1 operatively linked to a promoter.

5. The expression vector according to claim 4, wherein the promoter is devoid of CpG.

6. The expression vector according to claim 4, wherein the promoter is an interferon inducible promoter.

7. The expression vector according to claim 4, wherein the promoter is inducible by an alpha interferon, a beta interferon or a lambda interferon.

8. The expression vector according to claim 4, wherein the promoter is an IL28 inducible promoter.

9. An isolated cell transformed with the nucleic acid molecule according to claim 1.

10. The cell according to claim 9, wherein the protein encoded by said nucleic acid molecule is secreted by the cell.

11. The cell according to claim 9 further comprising a reporter gene.

12. The cell according to claim 11, wherein the reporter gene is a secreted embryonic alkaline phosphatase (SEAP) reporter gene.

13. The cell according to claim 12, wherein the reporter gene is devoid of CpG.

14. A kit comprising:
    the nucleic acid molecule according to claim 1, an expression vector comprising the nucleic acid molecule, or an isolated cell transformed with the nucleic acid molecule or an expression vector comprising the nucleic acid molecule, and
    a substrate of the protein having luciferase activity encoded by the nucleic acid molecule.

15. The kit according to claim 14, wherein the nucleic acid molecule comprises the nucleic acid sequence set forth as SEQ ID NO: 1.

16. An isolated cell transformed with the expression vector according to claim 4.

17. The isolated nucleic acid molecule according to claim 1, wherein said protein having luciferase activity comprises an amino acid sequence having at least 98% identity to the amino acid sequence set forth as SEQ ID NO: 3.

18. The isolated nucleic acid molecule according to claim 1, wherein said protein having luciferase activity comprises the amino acid sequence set forth as SEQ ID NO: 3.

19. The isolated nucleic acid molecule according to claim 1, wherein the signal peptide comprises the sequence of amino acids 1-17 of SEQ ID NO: 2.

20. The isolated nucleic acid molecule according to claim 1, wherein said preprotein comprises the amino acid sequence set forth as SEQ ID NO: 2.

* * * * *